United States Patent
Suga et al.

(10) Patent No.: US 11,975,040 B2
(45) Date of Patent: May 7, 2024

(54) PLEXIN BINDING REGULATOR

(71) Applicants: The University of Tokyo, Tokyo (JP); Osaka University, Osaka (JP)

(72) Inventors: Hiroaki Suga, Tokyo (JP); Nasir Kato Bashiruddin, Tokyo (JP); Junichi Takagi, Osaka (JP); Yukiko Matsunaga, Osaka (JP)

(73) Assignees: The University of Tokyo, Tokyo (JP); Osaka University, Osaka (JP)

( * ) Notice: Subject to any disclaimer, the term of this patent is extended or adjusted under 35 U.S.C. 154(b) by 291 days.

(21) Appl. No.: 16/309,957

(22) PCT Filed: Jun. 16, 2017

(86) PCT No.: PCT/JP2017/022387
§ 371 (c)(1),
(2) Date: Apr. 21, 2019

(87) PCT Pub. No.: WO2017/217545
PCT Pub. Date: Dec. 21, 2017

(65) Prior Publication Data
US 2019/0247457 A1    Aug. 15, 2019

(30) Foreign Application Priority Data
Jun. 16, 2016  (JP) ................. 2016-120226

(51) Int. Cl.
| | | |
|---|---|---|
| A61K 38/02 | (2006.01) | |
| A61K 9/00 | (2006.01) | |
| A61K 38/04 | (2006.01) | |
| A61P 9/00 | (2006.01) | |
| A61P 19/00 | (2006.01) | |
| A61P 19/08 | (2006.01) | |
| A61P 25/28 | (2006.01) | |
| A61P 35/00 | (2006.01) | |
| A61P 43/00 | (2006.01) | |
| C07K 7/50 | (2006.01) | |

(52) U.S. Cl.
CPC ............ *A61K 38/02* (2013.01); *A61K 9/0019* (2013.01); *A61K 9/0053* (2013.01); *A61K 38/04* (2013.01); *A61P 19/00* (2018.01); *A61P 19/08* (2018.01); *A61P 25/28* (2018.01); *C07K 7/50* (2018.01); *A61P 43/00* (2018.01); *C07K 7/50* (2013.01)

(58) Field of Classification Search
CPC ...... A61K 38/02; A61K 38/04; A61K 9/0019; A61K 9/0053; A61P 19/00; A61P 19/08; A61P 25/28; A61P 35/00; A61P 43/00; C07K 7/50
See application file for complete search history.

(56) References Cited

U.S. PATENT DOCUMENTS

2014/0303358 A1    10/2014    Takayanagi

FOREIGN PATENT DOCUMENTS

| WO | 2012157237 A1 | 11/2012 | |
|---|---|---|---|
| WO | 2013019445 A1 | 2/2013 | |
| WO | 2014161781 A1 | 10/2014 | |
| WO | 2014209802 A1 | 12/2014 | |
| WO | WO-2014198834 A1 * | 12/2014 | ............... A61P 7/00 |
| WO | 2016054411 A1 | 4/2016 | |

OTHER PUBLICATIONS

Matthew R. Smith, Markers of bone metabolism in prostate cancer, Cancer Treatment Reviews (2006) 32, Suppl. 1, 23-26.*
Olaf Brauns, Differential responsiveness of CRF receptor subtypes to N-terminal truncation of peptidic ligands, Peptides 23 (2002) 881-888.*
Jingjing Xia,Semaphorin-Plexin Signaling Controls Mitotic Spindle Orientation during Epithelial Morphogenesis and Repair, Developmental Cell 33, 299-313, May 2015.*
Thomas Worzfeld, Semaphorins and plexins as therapeutic targets, Nature Reviews, vol. 13 | Aug. 2014 | 603-621.*
Bio-synthesis (Cyclic Peptide Synthesis, Biosynthesis, published on line Apr. 2014).*
Maria Carolina A. Luque,CD100 and plexins B2 and B1 mediate monocyte-endothelial cell adhesion and might take part in atherogenesis Molecular Immunology 67 (2015) 559-567.*
Tissue expression of PLXNB1—Summary—The Human Protein Atlas, accessed on Aug. 5, 2022, pp. 1-3.*
Cell Line-PLXNB1—Summary—The Human Protein Atlas, accessed on Aug. 8, 2022, pp. 1-2.*
Hogan, et al., "Mapping the binding site of melanocortin 4 receptor agonists: a hydrophobic pocket formed by I3.28 (125), I3.32(129), and I7.42(291) is critical for . . . ", Feb. 9, 2006, pp. 911-922, vol. 49, No. 3, Publisher: J Med Chem.
Argast, et al., "Plexin B1 is repressed by oncogenic B-Raf signaling and functions as a tumor suppressor in melanoma cells", Jul. 30, 2009, pp. 2697-2709, vol. 28, No. 30, Publisher: Oncogene.
Basile, et al., "Class IV semaphorins promote angiogenesis by stimulating Rho-initiated pathways through plexin-B", Aug. 1, 2004, pp. 5212-5224, vol. 64, No. 15, Publisher: Cancer Res.

(Continued)

*Primary Examiner* — Julie Ha
*Assistant Examiner* — Erinne R Dabkowski
(74) *Attorney, Agent, or Firm* — Suzannah K. Sundby, Esq.; Canady + Lortz LLP

(57) ABSTRACT

The present invention provides a Plexin-binding regulating agent containing a cyclic peptide having an Arg-Trp-Thr structure or a Leu-Ser-Trp structure or a pharmaceutically acceptable salt of the cyclic peptide.

9 Claims, 13 Drawing Sheets
Specification includes a Sequence Listing.

(56) References Cited

OTHER PUBLICATIONS

Capparuccia, et al., "Semaphorin signaling in cancer cells and in cells of the tumor microenvironment—two sides of a coin", Jun. 1, 2009, pp. 1723-1736, vol. 122, No. Pt 11, Publisher: J Cell Sci.
Chabbert-De Ponnat, et al., "Soluble CD100 functions on human monocytes and immature dendritic cells require plexin C1 and plexin B1, respectively", Mar. 3, 2005, pp. 439-447, vol. 17, No. 4, Publisher: Int Immunol.
Ch'ng, et al., "Roles of Sema4D and Plexin-B1 in tumor progression", Sep. 21, 2010, vol. 9, No. 251, Publisher: Mol Cancer.
Conrotto, et al., "Sema4D induces angiogenesis through Met recruitment by Plexin B1", Jun. 1, 2005, pp. 4321-4329, vol. 105, No. 11, Publisher: Blood.
Granziero, et al., "CD100/Plexin-B1 interactions sustain proliferation and survival of normal and leukemic CD5+ B lymphocytes", Mar. 1, 2003, pp. 1962-1969, vol. 101, No. 5, Publisher: Blood.
Janssen, et al., "Structural basis of semaphorinplexin signalling", Sep. 26, 2010, pp. 1118-1122, vol. 467, No. 7319, Publisher: Nature.
Matsunaga, et al., "Allosteric Inhibition of a Semaphorin 4D Receptor Plexin B1 by a High-Affinity Macrocyclic Peptide", Nov. 17, 2016, pp. 1341-1350, vol. 23, No. 11, Publisher: Cell Chem Biol.
Negishi-Koga, et al., "Suppression of bone formation by osteoclastic expression of semaphorin 4D", Oct. 23, 2011, pp. 1473-1480, vol. 17, No. 11, Publisher: Nat Med.
Neufeld, et al., "The semaphorins: versatile regulators of tumour progression and tumour", Jun. 26, 2008, pp. 632-645, vol. 8, No. 8, Publisher: Nat Rev Cancer.
Okuno, et al., "Roles of Sema4D-plexin-B1 interactions in the central nervous system for pathogenesis of experimental autoimmune encephalomyelitis", Feb. 1, 2010, pp. 1499-1506, vol. 184, No. 3, Publisher: J Immunol.
Rody, et al., "Poor outcome in estrogen receptor-positive breast cancers predicted by loss of plexin B1", Feb. 15, 2007, pp. 1115-1122, vol. 13, No. 4, Publisher: Clin Cancer Res.
Suzuki, et al., "Semaphorins and their receptors in immune cell interactions", Dec. 17, 2007, pp. 17-23, vol. 9, No. 1, Publisher: Nat Immunol.
Swiercz, et al., "ErbB-2 and met reciprocally regulate cellular signaling via plexin-B1.", Jan. 25, 2008, pp. 1893-1901, vol. 283, No. 4, Publisher: J Biol Chem.
Wong, et al., "Plexin-B1 mutations in prostate cancer", Nov. 27, 2007, pp. 19040-19045, vol. 104, No. 48, Publisher: PNAS USA.
Worzfeld, et al., "Semaphorins and plexins as therapeutic targets", Aug. 2014, pp. 603-621, vol. 13, No. 8, Publisher: Nat Rev Drug Discov.
International Search Report received in PCT/JP2017/022387 dated Aug. 8, 2017.
Written Opinion received in PCT/JP2017/022387 dated Aug. 8, 2017.

\* cited by examiner

FIG. 6

FIG. 10
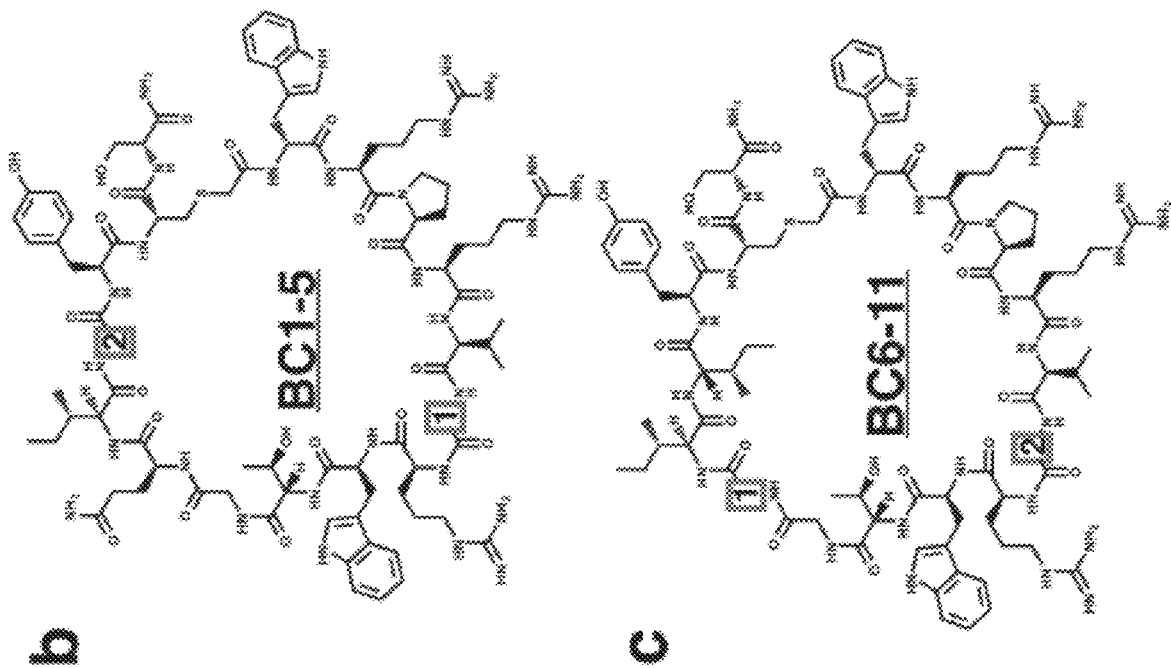
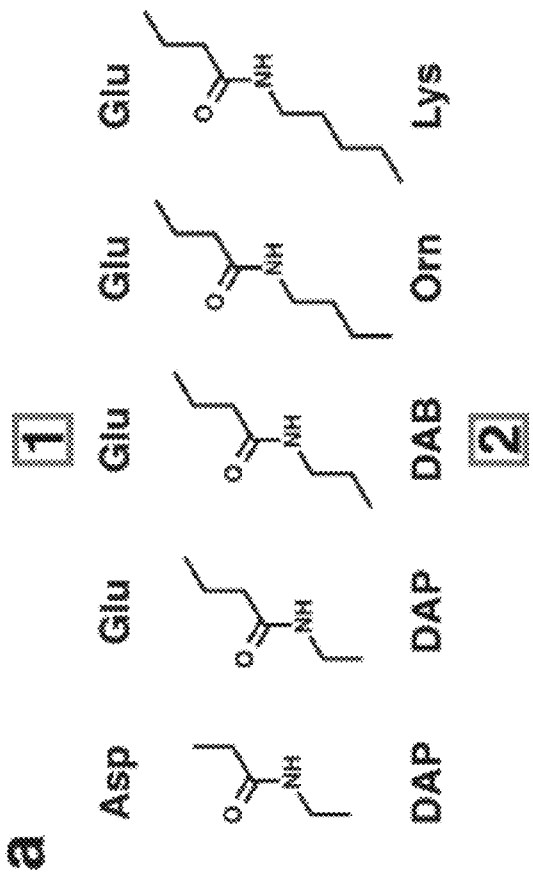

SEQUENCE LISTING

```
<160> NUMBER OF SEQ ID NOS: 58

<210> SEQ ID NO 1
<211> LENGTH: 5
<212> TYPE: PRT
<213> ORGANISM: Artificial Sequence
<220> FEATURE:
<223> OTHER INFORMATION: partial structure of cyclic peptide
<220> FEATURE:
<221> NAME/KEY: misc_feature
<222> LOCATION: (1)..(1)
<223> OTHER INFORMATION: Xaa is Val or Ile
<220> FEATURE:
<221> NAME/KEY: misc_feature
<222> LOCATION: (2)..(2)
<223> OTHER INFORMATION: Xaa can be any amino acid

<400> SEQUENCE: 1

Xaa Xaa Arg Trp Thr
1               5

<210> SEQ ID NO 2
<211> LENGTH: 6
<212> TYPE: PRT
<213> ORGANISM: Artificial Sequence
<220> FEATURE:
<223> OTHER INFORMATION: partial structure of cyclic peptide
<220> FEATURE:
<221> NAME/KEY: misc_feature
<222> LOCATION: (4)..(5)
<223> OTHER INFORMATION: Xaa can be any amino acid
```

```
<220> FEATURE:
<221> NAME/KEY: misc_feature
<222> LOCATION: (6)..(6)
<223> OTHER INFORMATION: Xaa is Ile, Val or Leu

<400> SEQUENCE: 2

Arg Trp Thr Xaa Xaa Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: partial structure of cyclic peptide

<400> SEQUENCE: 3

Leu Ser Trp Gln Thr Tyr Ser
1               5

<210> SEQ ID NO 4
<211> LENGTH: 5
<212> TYPE: PRT
<213> ORGANISM: Artificial Sequence
<220> FEATURE:
<223> OTHER INFORMATION: cyclic peptide
<220> FEATURE:
<221> NAME/KEY: misc_feature
<222> LOCATION: (1)..(1)
<223> OTHER INFORMATION: Xaa can be any amino acid
<220> FEATURE:
<221> NAME/KEY: misc_feature
<222> LOCATION: (5)..(5)
<223> OTHER INFORMATION: Xaa can be any amino acid

<400> SEQUENCE: 4

Xaa Arg Trp Thr Xaa
1               5

<210> SEQ ID NO 5
<211> LENGTH: 8
<212> TYPE: PRT
<213> ORGANISM: Artificial Sequence
<220> FEATURE:
<223> OTHER INFORMATION: partial structure of cyclic peptide
<220> FEATURE:
<221> NAME/KEY: misc_feature
<222> LOCATION: (1)..(1)
<223> OTHER INFORMATION: Xaa is Val or Ile
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (6)..(7)
<223> OTHER INFORMATION: Xaa can be any amino acid
<220> FEATURE:
<221> NAME/KEY: misc_feature
<222> LOCATION: (8)..(8)
<223> OTHER INFORMATION: Xaa is Ile, Val or Leu

<400> SEQUENCE: 5

Xaa Xaa Arg Trp Thr Xaa Xaa Xaa
1               5

<210> SEQ ID NO 6
<211> LENGTH: 5
<212> TYPE: PRT
<213> ORGANISM: Artificial Sequence
<220> FEATURE:
```

```
<223> OTHER INFORMATION: cyclic peptide
<220> FEATURE:
<221> NAME/KEY: misc_feature
<222> LOCATION: (1)..(1)
<223> OTHER INFORMATION: Xaa can be any amino acid
<220> FEATURE:
<221> NAME/KEY: misc_feature
<222> LOCATION: (5)..(5)
<223> OTHER INFORMATION: Xaa can be any amino acid

<400> SEQUENCE: 6

Xaa Leu Ser Trp Xaa
1               5

<210> SEQ ID NO 7
<211> LENGTH: 8
<212> TYPE: PRT
<213> ORGANISM: Artificial Sequence
<220> FEATURE:
<223> OTHER INFORMATION: cyclic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: THIOETH
<222> LOCATION: (1)..(1)
<220> FEATURE:
<221> NAME/KEY: misc_feature
<222> LOCATION: (1)..(1)
<223> OTHER INFORMATION: Xaa can be any amino acid
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (6)..(6)
<223> OTHER INFORMATION: Xaa can be any amino acid
<220> FEATURE:
<221> NAME/KEY: THIOETH
<222> LOCATION: (7)..(7)
<220> FEATURE:
<221> NAME/KEY: misc_feature
<222> LOCATION: (8)..(8)
<223> OTHER INFORMATION: Xaa can be any amino acid

<400> SEQUENCE: 7

Xaa Xaa Arg Trp Thr Xaa Cys Xaa
1               5

<210> SEQ ID NO 8
<211> LENGTH: 8
<212> TYPE: PRT
<213> ORGANISM: Artificial Sequence
<220> FEATURE:
<223> OTHER INFORMATION: cyclic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: THIOETH
<222> LOCATION: (1)..(1)
<220> FEATURE:
<221> NAME/KEY: misc_feature
<222> LOCATION: (1)..(1)
<223> OTHER INFORMATION: Xaa can be any amino acid
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (6)..(6)
```

```
<223> OTHER INFORMATION: Xaa can be any amino acid
<220> FEATURE:
<221> NAME/KEY: THIOETH
<222> LOCATION: (7)..(7)
<220> FEATURE:
<221> NAME/KEY: misc_feature
<222> LOCATION: (8)..(8)
<223> OTHER INFORMATION: Xaa can be any amino acid

<400> SEQUENCE: 8

Xaa Xaa Leu Ser Trp Xaa Cys Xaa
1               5

<210> SEQ ID NO 9
<211> LENGTH: 13
<212> TYPE: PRT
<213> ORGANISM: Artificial Sequence
<220> FEATURE:
<223> OTHER INFORMATION: cyclic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: THIOETH
<222> LOCATION: (1)..(1)
<220> FEATURE:
<221> NAME/KEY: misc_feature
<222> LOCATION: (1)..(1)
<223> OTHER INFORMATION: Xaa can be any amino acid
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (3)..(3)
<223> OTHER INFORMATION: Xaa is Val or Ile
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (8)..(9)
<223> OTHER INFORMATION: Xaa can be any amino acid
<220> FEATURE:
<221> NAME/KEY: misc_feature
<222> LOCATION: (10)..(10)
<223> OTHER INFORMATION: Xaa is Ile, Val or Leu
<220> FEATURE:
<221> NAME/KEY: misc_feature
<222> LOCATION: (11)..(11)
<223> OTHER INFORMATION: Xaa can be any amino acid
<220> FEATURE:
<221> NAME/KEY: THIOETH
<222> LOCATION: (12)..(12)
<220> FEATURE:
<221> NAME/KEY: misc_feature
<222> LOCATION: (13)..(13)
<223> OTHER INFORMATION: Xaa can be any amino acid

<400> SEQUENCE: 9

Xaa Xaa Xaa Xaa Arg Trp Thr Xaa Xaa Xaa Cys Xaa
1               5                   10

<210> SEQ ID NO 10
<211> LENGTH: 13
<212> TYPE: PRT
<213> ORGANISM: Artificial Sequence
<220> FEATURE:
<223> OTHER INFORMATION: cyclic peptide
<220> FEATURE:
<221> NAME/KEY: MOD_RES
<222> LOCATION: (1)..(1)
```

-continued

```
<223> OTHER INFORMATION: ACETYLATION
<220> FEATURE:
<221> NAME/KEY: THIOETH
<222> LOCATION: (1)..(1)
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (3)..(3)
<223> OTHER INFORMATION: Xaa is Val or Ile
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (8)..(9)
<223> OTHER INFORMATION: Xaa can be any amino acid
<220> FEATURE:
<221> NAME/KEY: misc_feature
<222> LOCATION: (10)..(10)
<223> OTHER INFORMATION: Xaa is Ile, Val or Leu
<220> FEATURE:
<221> NAME/KEY: misc_feature
<222> LOCATION: (11)..(11)
<223> OTHER INFORMATION: Xaa can be any amino acid
<220> FEATURE:
<221> NAME/KEY: THIOETH
<222> LOCATION: (12)..(12)
<220> FEATURE:
<221> NAME/KEY: misc_feature
<222> LOCATION: (13)..(13)
<223> OTHER INFORMATION: Xaa can be any amino acid

<400> SEQUENCE: 10

Trp Xaa Xaa Xaa Arg Trp Thr Xaa Xaa Xaa Xaa Cys Xaa
1               5                   10

<210> SEQ ID NO 11
<211> LENGTH: 12
<212> TYPE: PRT
<213> ORGANISM: Artificial Sequence
<220> FEATURE:
<223> OTHER INFORMATION: cyclic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: THIOETH
<222> LOCATION: (1)..(1)
<220> FEATURE:
<221> NAME/KEY: misc_feature
<222> LOCATION: (1)..(1)
<223> OTHER INFORMATION: Xaa can be any amino acid
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (10)..(10)
<223> OTHER INFORMATION: Xaa can be any amino acid
<220> FEATURE:
<221> NAME/KEY: THIOETH
<222> LOCATION: (11)..(11)
<220> FEATURE:
<221> NAME/KEY: misc_feature
<222> LOCATION: (12)..(12)
<223> OTHER INFORMATION: Xaa can be any amino acid

<400> SEQUENCE: 11

Xaa Xaa Leu Ser Trp Gln Thr Tyr Ser Xaa Cys Xaa
1               5                   10
```

```
<210> SEQ ID NO 12
<211> LENGTH: 12
<212> TYPE: PRT
<213> ORGANISM: Artificial Sequence
<220> FEATURE:
<223> OTHER INFORMATION: cyclic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: THIOETH
<222> LOCATION: (1)..(1)
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (10)..(10)
<223> OTHER INFORMATION: Xaa can be any amino acid
<220> FEATURE:
<221> NAME/KEY: THIOETH
<222> LOCATION: (11)..(11)
<220> FEATURE:
<221> NAME/KEY: misc_feature
<222> LOCATION: (12)..(12)
<223> OTHER INFORMATION: Xaa can be any amino acid

<400> SEQUENCE: 12

Trp Xaa Leu Ser Trp Gln Thr Tyr Ser Xaa Cys Xaa
1               5                  10

<210> SEQ ID NO 13
<211> LENGTH: 13
<212> TYPE: PRT
<213> ORGANISM: Artificial Sequence
<220> FEATURE:
<223> OTHER INFORMATION: variable region of cyclic peptide

<400> SEQUENCE: 13

Arg Pro Arg Val Ala Arg Trp Thr Gly Gln Ile Ile Tyr
1               5                  10

<210> SEQ ID NO 14
<211> LENGTH: 12
<212> TYPE: PRT
<213> ORGANISM: Artificial Sequence
<220> FEATURE:
<223> OTHER INFORMATION: variable region of cyclic peptide

<400> SEQUENCE: 14

Arg Val Arg Val Glu Arg Trp Thr Gly Lys Leu Ile
1               5                  10

<210> SEQ ID NO 15
<211> LENGTH: 13
<212> TYPE: PRT
<213> ORGANISM: Artificial Sequence
<220> FEATURE:
<223> OTHER INFORMATION: variable region of cyclic peptide

<400> SEQUENCE: 15

Arg Pro Arg Val Ala Arg Trp Thr Gly Gln Ile Ile His
1               5                  10

<210> SEQ ID NO 16
<211> LENGTH: 13
<212> TYPE: PRT
```

<213> ORGANISM: Artificial Sequence
<220> FEATURE:
<223> OTHER INFORMATION: variable region of cyclic peptide

<400> SEQUENCE: 16

Arg Pro Arg Val Ala Arg Trp Thr Gly Gln Val Ile Tyr
1               5                   10

<210> SEQ ID NO 17
<211> LENGTH: 13
<212> TYPE: PRT
<213> ORGANISM: Artificial Sequence
<220> FEATURE:
<223> OTHER INFORMATION: variable region of cyclic peptide

<400> SEQUENCE: 17

Arg Pro Arg Val Ala Arg Trp Thr Gly Gln Asn Ile Tyr
1               5                   10

<210> SEQ ID NO 18
<211> LENGTH: 13
<212> TYPE: PRT
<213> ORGANISM: Artificial Sequence
<220> FEATURE:
<223> OTHER INFORMATION: variable region of cyclic peptide

<400> SEQUENCE: 18

Arg Pro Arg Val Ala Arg Trp Thr Gly Gln Ile Ser Asn
1               5                   10

<210> SEQ ID NO 19
<211> LENGTH: 13
<212> TYPE: PRT
<213> ORGANISM: Artificial Sequence
<220> FEATURE:
<223> OTHER INFORMATION: variable region of cyclic peptide

<400> SEQUENCE: 19

Arg Pro Arg Val Ala Arg Trp Thr Gly Gln Ile Ile Asn
1               5                   10

<210> SEQ ID NO 20
<211> LENGTH: 13
<212> TYPE: PRT
<213> ORGANISM: Artificial Sequence
<220> FEATURE:
<223> OTHER INFORMATION: variable region of cyclic peptide

<400> SEQUENCE: 20

Arg Pro Arg Ala Ala Arg Trp Thr Gly Gln Ile Ile Tyr
1               5                   10

<210> SEQ ID NO 21
<211> LENGTH: 13
<212> TYPE: PRT
<213> ORGANISM: Artificial Sequence
<220> FEATURE:
<223> OTHER INFORMATION: variable region of cyclic peptide

<400> SEQUENCE: 21

Arg Pro Tyr Ile Glu Arg Trp Thr Gly Arg Leu Ile Val
1               5                   10

<210> SEQ ID NO 22
<211> LENGTH: 13
<212> TYPE: PRT
<213> ORGANISM: Artificial Sequence

```
<220> FEATURE:
<223> OTHER INFORMATION: variable region of cyclic peptide

<400> SEQUENCE: 22

Arg Trp Phe Tyr Asp Arg Trp Thr Gly Thr Phe Tyr Val
1               5                   10

<210> SEQ ID NO 23
<211> LENGTH: 13
<212> TYPE: PRT
<213> ORGANISM: Artificial Sequence
<220> FEATURE:
<223> OTHER INFORMATION: variable region of cyclic peptide

<400> SEQUENCE: 23

Arg Ala Phe Ile Glu Arg Trp Thr Gly Arg Leu Val Val
1               5                   10

<210> SEQ ID NO 24
<211> LENGTH: 13
<212> TYPE: PRT
<213> ORGANISM: Artificial Sequence
<220> FEATURE:
<223> OTHER INFORMATION: variable region of cyclic peptide

<400> SEQUENCE: 24

Leu Gly Tyr Ile Ala Arg Trp Thr Gly Thr Val Val Lys
1               5                   10

<210> SEQ ID NO 25
<211> LENGTH: 13
<212> TYPE: PRT
<213> ORGANISM: Artificial Sequence
<220> FEATURE:
<223> OTHER INFORMATION: variable region of cyclic peptide

<400> SEQUENCE: 25

Leu Ala Tyr Ile Glu Arg Trp Thr Gly Gln Ile Val Arg
1               5                   10

<210> SEQ ID NO 26
<211> LENGTH: 13
<212> TYPE: PRT
<213> ORGANISM: Artificial Sequence
<220> FEATURE:
<223> OTHER INFORMATION: variable region of cyclic peptide

<400> SEQUENCE: 26

Asn Ser Asn Val Leu Ser Trp Gln Thr Tyr Ser Trp Tyr
1               5                   10

<210> SEQ ID NO 27
<211> LENGTH: 12
<212> TYPE: PRT
<213> ORGANISM: Artificial Sequence
<220> FEATURE:
<223> OTHER INFORMATION: variable region of cyclic peptide

<400> SEQUENCE: 27

Asn Gly Arg Leu Ser Trp Gln Thr Tyr Ser His Leu
1               5                   10

<210> SEQ ID NO 28
<211> LENGTH: 14
<212> TYPE: PRT
<213> ORGANISM: Artificial Sequence
<220> FEATURE:
```

<223> OTHER INFORMATION: variable region of cyclic peptide

<400> SEQUENCE: 28

Ala Val Ser Asn Pro Pro Arg Pro His Tyr Ile Thr Ile Glu
1               5                   10

<210> SEQ ID NO 29
<211> LENGTH: 10
<212> TYPE: PRT
<213> ORGANISM: Artificial Sequence
<220> FEATURE:
<223> OTHER INFORMATION: variable region of cyclic peptide

<400> SEQUENCE: 29

Leu Ser Trp Gln Ala Tyr Ser Trp Gly Gln
1               5                   10

<210> SEQ ID NO 30
<211> LENGTH: 13
<212> TYPE: PRT
<213> ORGANISM: Artificial Sequence
<220> FEATURE:
<223> OTHER INFORMATION: variable region of cyclic peptide

<400> SEQUENCE: 30

Arg Pro Arg Val Ala Arg Trp Thr Gly Gln Ile Ile Tyr
1               5                   10

<210> SEQ ID NO 31
<211> LENGTH: 12
<212> TYPE: PRT
<213> ORGANISM: Artificial Sequence
<220> FEATURE:
<223> OTHER INFORMATION: variable region of cyclic peptide

<400> SEQUENCE: 31

Arg Val Arg Val Glu Arg Trp Thr Gly Lys Leu Ile
1               5                   10

<210> SEQ ID NO 32
<211> LENGTH: 13
<212> TYPE: PRT
<213> ORGANISM: Artificial Sequence
<220> FEATURE:
<223> OTHER INFORMATION: variable region of cyclic peptide

<400> SEQUENCE: 32

Arg Pro Arg Val Ala Arg Trp Thr Gly Gln Ile Ile His
1               5                   10

<210> SEQ ID NO 33
<211> LENGTH: 13
<212> TYPE: PRT
<213> ORGANISM: Artificial Sequence
<220> FEATURE:
<223> OTHER INFORMATION: variable region of cyclic peptide

<400> SEQUENCE: 33

Arg Pro Arg Val Ala Arg Trp Thr Gly Gln Val Ile Tyr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: variable region of cyclic peptide

```
<400> SEQUENCE: 34

Arg Pro Arg Val Ala Arg Trp Thr Gly Asn Ile Tyr
1               5                   10

<210> SEQ ID NO 35
<211> LENGTH: 13
<212> TYPE: PRT
<213> ORGANISM: Artificial Sequence
<220> FEATURE:
<223> OTHER INFORMATION: variable region of cyclic peptide

<400> SEQUENCE: 35

Arg Pro Arg Val Ala Arg Trp Thr Gly Gln Ile Ser Tyr
1               5                   10

<210> SEQ ID NO 36
<211> LENGTH: 13
<212> TYPE: PRT
<213> ORGANISM: Artificial Sequence
<220> FEATURE:
<223> OTHER INFORMATION: variable region of cyclic peptide

<400> SEQUENCE: 36

Arg Pro Arg Val Ala Arg Trp Thr Gly Gln Ile Ile Asn
1               5                   10

<210> SEQ ID NO 37
<211> LENGTH: 13
<212> TYPE: PRT
<213> ORGANISM: Artificial Sequence
<220> FEATURE:
<223> OTHER INFORMATION: variable region of cyclic peptide

<400> SEQUENCE: 37

Arg Pro Arg Ala Ala Arg Trp Thr Gly Gln Ile Ile Tyr
1               5                   10

<210> SEQ ID NO 38
<211> LENGTH: 13
<212> TYPE: PRT
<213> ORGANISM: Artificial Sequence
<220> FEATURE:
<223> OTHER INFORMATION: variable region of cyclic peptide

<400> SEQUENCE: 38

Asn Ser Asn Val Leu Ser Trp Gln Thr Tyr Ser Trp Tyr
1               5                   10

<210> SEQ ID NO 39
<211> LENGTH: 12
<212> TYPE: PRT
<213> ORGANISM: Artificial Sequence
<220> FEATURE:
<223> OTHER INFORMATION: variable region of cyclic peptide

<400> SEQUENCE: 39

Asn Gly Thr Leu Ser Trp Gln Thr Tyr Ser His Leu
1               5                   10

<210> SEQ ID NO 40
<211> LENGTH: 15
<212> TYPE: PRT
<213> ORGANISM: Artificial Sequence
<220> FEATURE:
<223> OTHER INFORMATION: variable region of cyclic peptide
```

-continued

```
<400> SEQUENCE: 40

Ala Val Ser Asn Leu Pro Pro Arg Pro His Ile Thr Tyr Ile Glu
1               5                   10                  15

<210> SEQ ID NO 41
<211> LENGTH: 10
<212> TYPE: PRT
<213> ORGANISM: Artificial Sequence
<220> FEATURE:
<223> OTHER INFORMATION: variable region of cyclic peptide

<400> SEQUENCE: 41

Leu Ser Trp Gln Ala Tyr Ser Trp Gly Gln
1               5                   10

<210> SEQ ID NO 42
<211> LENGTH: 5
<212> TYPE: PRT
<213> ORGANISM: Artificial Sequence
<220> FEATURE:
<223> OTHER INFORMATION: Plexin-binding regulating agent
<220> FEATURE:
<221> NAME/KEY: MISC_FEATURE
<222> LOCATION: (1)..(1)
<223> OTHER INFORMATION: Wherein Xaa is Val or Ile
<220> FEATURE:
<221> NAME/KEY: MISC_FEATURE
<222> LOCATION: (2)..(2)
<223> OTHER INFORMATION: Wherein Xaa is any amino acid

<400> SEQUENCE: 42

Xaa Xaa Arg Trp Thr
1               5

<210> SEQ ID NO 43
<211> LENGTH: 6
<212> TYPE: PRT
<213> ORGANISM: Artificial Sequence
<220> FEATURE:
<223> OTHER INFORMATION: Plexin-binding regulating agent
<220> FEATURE:
<221> NAME/KEY: MISC_FEATURE
<222> LOCATION: (4)..(4)
<223> OTHER INFORMATION: Wherein Xaa is any amino acid
<220> FEATURE:
<221> NAME/KEY: MISC_FEATURE
<222> LOCATION: (5)..(5)
<223> OTHER INFORMATION: Wherein Xaa is any amino acid
<220> FEATURE:
<221> NAME/KEY: MISC_FEATURE
<222> LOCATION: (6)..(6)
<223> OTHER INFORMATION: Wherein Xaa is Ile, Val, or Leu

<400> SEQUENCE: 43

Arg Trp Thr Xaa Xaa Xaa
1               5

<210> SEQ ID NO 44
<211> LENGTH: 8
<212> TYPE: PRT
<213> ORGANISM: Artificial Sequence
<220> FEATURE:
<223> OTHER INFORMATION: Plexin-binding regulating agent
<220> FEATURE:
<221> NAME/KEY: MISC_FEATURE
<222> LOCATION: (1)..(1)
<223> OTHER INFORMATION: Wheren Xaa is Val or Ile
<220> FEATURE:
<221> NAME/KEY: MISC_FEATURE
<222> LOCATION: (2)..(2)
<223> OTHER INFORMATION: Wheren Xaa is any amino acid
```

```
<220> FEATURE:
<221> NAME/KEY: MISC_FEATURE
<222> LOCATION: (6)..(6)
<223> OTHER INFORMATION: Wheren Xaa is any amino acid
<220> FEATURE:
<221> NAME/KEY: MISC_FEATURE
<222> LOCATION: (7)..(7)
<223> OTHER INFORMATION: Wheren Xaa is any amino acid
<220> FEATURE:
<221> NAME/KEY: MISC_FEATURE
<222> LOCATION: (8)..(8)
<223> OTHER INFORMATION: Wheren Xaa is Ile, Val, or Leu

<400> SEQUENCE: 44

Xaa Xaa Arg Trp Thr Xaa Xaa Xaa
1               5

<210> SEQ ID NO 45
<211> LENGTH: 7
<212> TYPE: PRT
<213> ORGANISM: Artificial Sequence
<220> FEATURE:
<223> OTHER INFORMATION: Plexin-binding regulating agent

<400> SEQUENCE: 45

Leu Ser Trp Gln Thr Tyr Ser
1               5

<210> SEQ ID NO 46
<211> LENGTH: 13
<212> TYPE: PRT
<213> ORGANISM: Artificial Sequence
<220> FEATURE:
<223> OTHER INFORMATION: Plexin-binding regulating agent

<400> SEQUENCE: 46

Arg Pro Arg Val Ala Arg Trp Thr Gly Gln Ile Ser Asn
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Plexin-binding regulating agent

<400> SEQUENCE: 47

Arg Pro Tyr Ile Glu Arg Trp Thr Gly Arg Leu Ile Val
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Plexin-binding regulating agent

<400> SEQUENCE: 48

Arg Trp Phe Tyr Asp Arg Trp Thr Gly Thr Phe Tyr Val
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Plexin-binding regulating agent

<400> SEQUENCE: 49
```

```
Arg Ala Phe Ile Glu Arg Trp Thr Gly Arg Leu Val Val
1               5                   10
```

<210> SEQ ID NO 50
<211> LENGTH: 13
<212> TYPE: PRT
<213> ORGANISM: Artificial Sequence
<220> FEATURE:
<223> OTHER INFORMATION: Plexin-binding regulating agent

<400> SEQUENCE: 50

```
Leu Gly Tyr Ile Ala Arg Trp Thr Gly Thr Val Val Lys
1               5                   10
```

<210> SEQ ID NO 51
<211> LENGTH: 13
<212> TYPE: PRT
<213> ORGANISM: Artificial Sequence
<220> FEATURE:
<223> OTHER INFORMATION: Plexin-binding regulating agent

<400> SEQUENCE: 51

```
Leu Ala Tyr Ile Glu Arg Trp Thr Gly Gln Ile Val Arg
1               5                   10
```

<210> SEQ ID NO 52
<211> LENGTH: 12
<212> TYPE: PRT
<213> ORGANISM: Artificial Sequence
<220> FEATURE:
<223> OTHER INFORMATION: Plexin-binding regulating agent

<400> SEQUENCE: 52

Asn Gly Arg Leu Ser Trp Gln Thr Tyr Ser His Leu
1 5 10

<210> SEQ ID NO 53
<211> LENGTH: 15
<212> TYPE: PRT
<213> ORGANISM: Artificial Sequence
<220> FEATURE:
<223> OTHER INFORMATION: Plexin-binding regulating agent

<400> SEQUENCE: 53

Trp Arg Pro Arg Val Ala Arg Trp Thr Gly Gln Ile Ile Tyr Cys
1 5 10 15

<210> SEQ ID NO 54
<211> LENGTH: 15
<212> TYPE: PRT
<213> ORGANISM: Artificial Sequence
<220> FEATURE:
<223> OTHER INFORMATION: Plexin-binding regulating agent

<400> SEQUENCE: 54

Trp Arg Pro Tyr Ile Glu Arg Trp Thr Gly Arg Leu Ile Val Cys
1 5 10 15

<210> SEQ ID NO 55
<211> LENGTH: 15
<212> TYPE: PRT
<213> ORGANISM: Artificial Sequence
<220> FEATURE:
<223> OTHER INFORMATION: Plexin-binding regulating agent

<400> SEQUENCE: 55

-continued

```
Trp Arg Trp Phe Tyr Asp Arg Trp Thr Gly Thr Phe Tyr Val Cys
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Plexin-binding regulating agent

<400> SEQUENCE: 56

Trp Arg Ala Phe Ile Glu Arg Trp Thr Gly Arg Leu Val Val Cys
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Plexin-binding regulating agent

<400> SEQUENCE: 57

Trp Leu Gly Tyr Ile Ala Arg Trp Thr Gly Thr Val Val Lys Cys
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Plexin-binding regulating agent

<400> SEQUENCE: 58

Trp Leu Ala Tyr Ile Glu Arg Trp Thr Gly Gln Ile Val Arg Cys
1               5                   10                  15
```

PLEXIN BINDING REGULATOR

REFERENCE TO A SEQUENCE LISTING SUBMITTED VIA EFS-WEB

The content of the ASCII text file of the sequence listing named "20211030_034574_017US1_subseq_ST25" which is 18.1 kb in size was created on Oct. 30, 2021 and electronically submitted via EFS-Web on Oct. 30, 2021 is incorporated herein by reference in its entirety.

TECHNICAL FIELD

The present invention relates to a Plexin-binding regulating agent.

BACKGROUND ART

Semaphorin known as a nerve axon guidance factor is a highly functional protein having an important role in growth of neuronal cells, immunoresponse, bone metabolism, differentiation of cancer cells, organogenesis, and the like. In mammals, Semaphorin 3A to 3G, 4A to 4G, 5A, 5B, 6A to 6D, and 7A are known.

Semaphorin and Plexin acting as a signal receptor therefor are important as a drug target of various diseases (Non-patent Documents 1 to 4).

Plexin which is a single-pass transmembrane protein having a molecular weight of 300 kDa or more is classified into nine groups A1 to A4, B1 to B3, C1, and D1 in mammals. Of these, Plexin A1 and Plexin B1 are known to be homologues to each other.

Of these nine Plexin groups, Plexin A1 interacts with Semaphorin 3A and Plexin B1 interacts with Semaphorin 4D and they have a regulatory role in various scenes of a biological process such as metabolism in bone tissues and growth of neuronal cells (Non-Patent Documents 4 and 5).

In the metabolism in bone tissues, Plexin is expressed on the surface of osteoblasts involved in osteogenesis and Semaphorin is expressed on the surface of osteoclasts involved in bone resorption.

Non-Patent Document 6 discloses an increase in bone quantity due to genetic knockout of Plexin in mice. The interaction between Plexin and Semaphorin is therefore considered to inhibit osteogenesis.

In the growth of neuronal cells, the interaction between Semaphorin and Plexin on the surface of neuronal cells is understood as a repulsive signal leading to cytoskeletal reorganization inducing collapse of a growth cone.

Further, it is described that neuroinflammation requires interaction between Plexin and Semaphorin in activated T cells and therefore, Plexin-deficient mice are protected from neuroinflammation (Non-Patent Document 7). Similar to Semaphorin, Plexin is expressed in various cells in neuroinflammation and it enhances differentiation of B cells (Non-Patent Documents 8 and 9).

It is reported that Plexin is also involved in cell functions such as cell migration and differentiation of cells and it is described in many documents that expression of Plexin is accelerated in various cancers (for example, Non-Patent Document 10). It is also described that the interaction between Plexin and Semaphorin is involved in angiogenesis, cell migration, or cell invasion in cancer (Non-Patent Documents 11 to 16).

The interaction between Plexin and Semaphorin has a variety of roles and Plexin can be a therapeutic target for the increase of a bone quantity in osteoporosis or the treatment of multiple sclerosis or the like or as a cancer metastasis inhibitor.

CITATION LIST

Non-Patent Documents

Non-Patent Document 1: Nat Rev Cancer, 2008, 8(8), 632-645
Non-Patent Document 2: Nat Immunol, 2008, 9(1), 17-23
Non-Patent Document 3: J Cell Sci, 122(Pt 11), 1723-1736
Non-Patent Document 4: Nat Rev Drug Discov, 2014, 13(8), 603-621
Non-Patent Document 5: Nature, 2010, 467(7319), 1118-1122
Non-Patent Document 6: Nat Med, 2011, 17(11), 1473-1480
Non-Patent Document 7: J Immunol, 2010, 184(3), 1499-1506
Non-Patent Document 8: Blood, 2003, 101(5), 1962-1969
Non-Patent Document 9: Int Immunol, 2005, 17(4), 439-447
Non-Patent Document 10: Mol Cancer, 2010, 9, 251
Non-Patent Document 11: Blood, 2005, 105(11), 4321-4329
Non-Patent Document 12: Cancer Res, 2004, 64(15), 5212-5224
Non-Patent Document 13: Oncogene, 2009, 28(30), 2697-2709
Non-Patent Document 14: J BiolChem, 2008, 283(4), 1893-1901
Non-Patent Document 15: Clin Cancer Res, 2007, 13(4), 1115-1122
Non-Patent Document 16: Proc Natl AcadSci USA, 2007, 104(48), 19040-19045

SUMMARY

Technical Problem

As described above, the interaction between Semaphorin and Plexin is a regulatory factor of, for example, differentiation of cancer cells, bone metabolism, neurodegeneration or neuroinflammation so that a Plexin-binding regulating agent is presumed to be usable for, for example, cancer therapy, therapy of diseases associated with bone metabolism, and therapy of neurodegenerative diseases or neuroinflammatory diseases.

The contact surface in the interaction between Semaphorin and Plexin is a wide and flat bonding surface so that it has been difficult to use it as a target of a conventional low-molecular drug.

The technical problem of the present invention is to provide a novel Plexin-binding regulating agent using a cyclic peptide.

Solution to Problem

The present inventors have carried out extensive research with a view to overcoming the above-described problem. As a result, it has been found that a cyclic peptide having a specific structure regulates binding of Plexin, leading to completion of the invention.

The present invention is as follows.
(1) A Plexin-binding regulating agent containing a cyclic peptide having an Arg-Trp-Thr structure or a Leu-Ser-Trp structure or a pharmaceutically acceptable salt of the cyclic peptide.

(2) The binding regulating agent as described in (1), wherein the cyclic peptide has a Val/Ile-Xaa1-Arg-Trp-Thr structure (SEQ ID NO: 42, wherein Xaa1 is an arbitrary amino acid).

(3) The binding regulating agent as described in (1) or (2), wherein the cyclic peptide has an Arg-Trp-Thr-Xaa2-Xaa3-Ile/Val/Leu structure (SEQ ID NO: 43, wherein Xaa2 and Xaa3 each independently represent an arbitrary amino acid).

(4) The binding regulating agent as described in (1), wherein the cyclic peptide has a Leu-Ser-Trp-Gln-Thr-Tyr-Ser structure (SEQ ID NO: 45).

(5) The binding regulating agent as described in any of (1) to (4), wherein the cyclic peptide has an N—CO—$CH_2$—S structure.

(6) The binding regulating agent as described in (5), wherein the N is derived from an amino group of tryptophan.

(7) The binding regulating agent as described in (5) or (6), wherein the S is derived from a thiol group of cysteine.

(8) The binding regulating agent described in any of (1) to (7), wherein the cyclic peptide has a cyclic structure having from 10 to 20 amino acids.

(9) The binding regulating agent as described in any of (1) to (8), wherein the cyclic peptide has an intramolecular lactam bridge structure.

(10) The binding regulating agent as described in any of (1) to (9), which is a dimer of the cyclic peptide.

(11) The binding regulating agent as described in any of (1) to (10), wherein Plexin is Plexin A1 or Plexin B1.

(12) The binding regulating agent as described in any of (1) to (11), wherein the binding regulating agent is between Semaphorin and Plexin and Semaphorin is Semaphorin 3A or Semaphorin 4D.

(13) The binding regulating agent as described in any of (1) to (12), wherein the binding regulating agent is between Semaphorin 4D and Plexin B1.

(14) A pharmaceutical composition containing the binding regulating agent as described in any of (1) to (13).

(15) The pharmaceutical composition as described in (14) for use in cancer therapy.

(16) The pharmaceutical composition as described in (14) for use in the treatment of a disease associated with bone metabolism.

(17) The pharmaceutical composition as described in (14) for use in the treatment of a neurodegenerative disease or a neuroinflammatory disease.

Advantageous Effects of Invention

The present invention makes it possible to provide a novel Plexin-binding regulating agent using a cyclic peptide.

BRIEF DESCRIPTION OF DRAWINGS

FIG. 1B shows the general formula of cyclic peptides and FIG. 1c shows the respective amino acid sequence of the cyclic peptides and their binding affinity to Plexin B1. The sequences from top to bottom are SEQ ID NO: 40, SEQ ID NO: 31, SEQ ID NO: 37, SEQ ID NO: 30, SEQ ID NO: 38, and SEQ ID NO: 39.

FIG. 6a is the structure of a cyclic peptide P6 and FIG. 6b shows the binding inhibition assay between Semaphorin 4D and Plexin B1 at various concentrations of P6.

FIG. 6c shows inhibition of growth cone collapse observed in FIG. 6b as a result of the addition of P6 which has occurred depending on Semaphorin 4D.

FIG. 10 shows a cyclic peptide having an intramolecular lactam bridge structure, in which Asp represents aspartic acid, Glu represents glutamic acid, DAP represents 2,3-diaminopropionic acid, DAB represents 2,4-diaminobutyric acid, Orn represents ornithine, and Lys represents lysine.

FIG. 12a shows P6dPEG11 and FIG. 12b shows P6dPEG5.

FIG. 13a shows the results of an inhibition test of Semaphorin 4D-dependent cell detachment. FIG. 13b shows comparison in binding affinity to Plexin B1 by using the SPR method.

DESCRIPTION OF EMBODIMENTS

Figure 1:
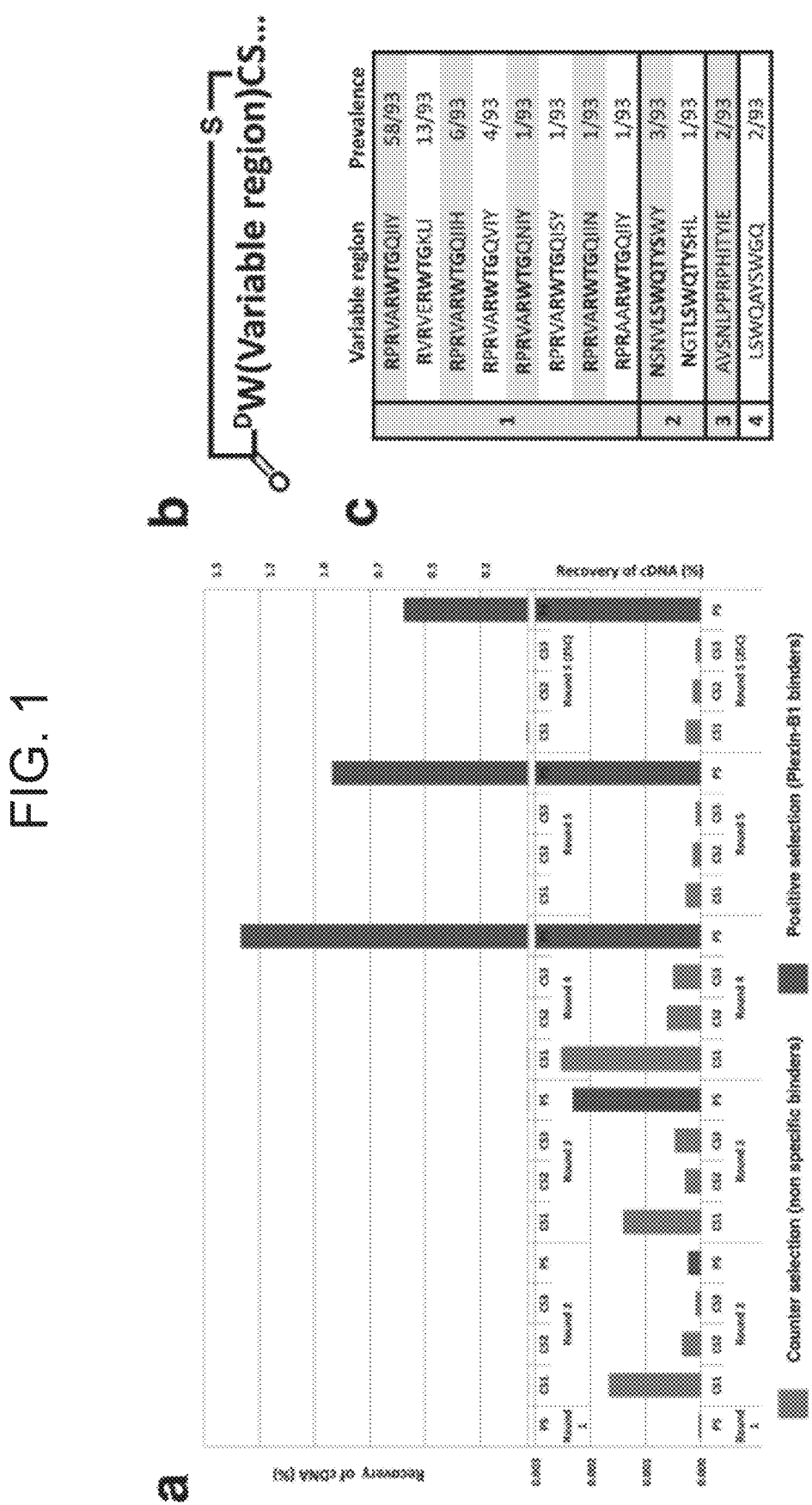
FIG. 1a shows one example of five selection results obtained by performing the RaPID system for Plexin B1.
FIG. 1b is the general formula of cyclic peptides and FIG. 1c shows the respective amino acid sequences of the cyclic peptides thus obtained. The sequences from top to bottom are SEQ ID NO: 30 to SEQ ID NO: 41, respectively.

The present invention will be described specifically by embodiments. The present invention is however not limited to or by the embodiments, but can be modified in various ways.

The details disclosed in the documents to be referred to in the present invention are incorporated herein as reference.

The Plexin-binding regulating agent of the present invention contains a cyclic peptide having an Arg-Trp-Thr structure or a Leu-Ser-Trp structure or a pharmaceutically acceptable salt of the cyclic peptide.

In the present invention, the cyclic peptide having an Arg-Trp-Thr structure or a Leu-Ser-Trp structure is presumed to bind to Plexin via the Arg-Trp-Thr structure to allosterically regulate the signal transmission between Semaphorin and Plexin. In particular, the binding regulating agent of the present invention preferably functions as a binding regulating agent of Plexin B1 and Plexin A1 which is a homologue thereof.

In the present specification, the term "cyclic peptide" means a cyclic peptide at least having, in the molecule thereof, a cyclic structure composed of four or more amino acids.

The cyclic peptide may have, as a molecular structure other than the cyclic structure, a linear structure in which amino acids are linked by peptide bonding or it may have a structure other than a peptide structure.

In the present specification, the term "cyclic structure" means, in a linear peptide, a closed-ring structure which is formed in the molecule by bonding, directly or via a linker or the like, of two amino acids separated by two or more amino acid residues.

In the present specification, the term "separated by two or more amino acid residues" means that the two amino acids have at least two amino acid residues therebetween.

The closed-ring structure in the cyclic structure is not particularly limited but it is formed by covalent bonding of two amino acids.

Examples of the covalent bonding between two amino acids include disulfide bonding, peptide bonding, alkyl bonding, alkenyl bonding, ester bonding, thioester bonding, ether bonding, thioether bonding, phosphonate ether bonding, azo bonding, C—S—C bonding, C—N—C bonding, C=N—C bonding, amide bonding, lactam bridging, carbamoyl bonding, urea bonding, thiourea bonding, amine bonding, and thioamide bonding.

A closed-ring structure is formed by peptide bonding when two amino acids bond to each other in the main chain of the amino acids, but a covalent bond between these two amino acids may be formed by bonding of the respective side chains of the two amino acids or bonding of the side chain and the main chain of them.

The cyclic structure is not limited to that formed by bonding of the N-terminal amino acid and the C-terminal amino acid of a linear peptide, but it may be formed by bonding of a terminal amino acid and a non-terminal amino acid or bonding of non-terminal amino acids. When one of the amino acids bonded for the formation of the cyclic structure is a terminal amino acid and the other one is a non-terminal amino acid, the resulting cyclic peptide has a cyclic structure having a linear peptide attached thereto like a tail.

The amino acid that forms a cyclic structure may be a naturally occurring amino acid and also an artificial amino acid variant or derivative. Examples include naturally occurring proteinogenic L-amino acids, non-naturally occurring amino acids, and chemically synthesized compounds having properties which are known in the art and characteristic of an amino acid.

The proteinogenic amino acids are, when represented by three-letter code known in the art, Arg, His, Lys, Asp, Glu, Ser, Thr, Asn, Gln, Cys, Gly, Pro, Ala, Ile, Leu, Met, Phe, Trp, Tyr, and Val.

The term "non-proteinogenic amino acids" means naturally occurring or non-naturally occurring amino acids other than proteinogenic amino acids.

Examples of the non-naturally occurring amino acids include α,α-disubstituted amino acids (such as α-methyl-alanine), N-alkyl-α-amino acids, D-amino acids, β-amino acids, and α-hydroxy acids, each having a main chain structure different from that of naturally occurring amino acids; amino acids (such as norleucine and homohistidine) having a side-chain structure different from that of naturally occurring amino acids; amino acids (such as "homo" amino acids, homophenylalanine, and homohistidine) having extra methylene in the side chain thereof; and amino acids (such as cysteic acid) obtained by substituting a carboxylic acid functional group in the side chain by a sulfonic acid group. Specific examples of the non-naturally occurring amino acids include amino acids described in WO2015/030014.

The number of amino acids constituting the cyclic structure is not particularly limited insofar as it is 4 or more. It may be, for example, 5 or more, 8 or more, or 10 or more and may be 30 or less, 25 or less, 20 or less, or 15 or less.

The number of amino acids constituting the cyclic structure is preferably 4 or more to 30 or less. Within a range of 4 or more to 30 or less, the number of amino acids constituting the cyclic structure may be set at 5 or more, 8 or more, or 10 or more and set at 30 or less, 25 or less, 20 or less, or 15 or less.

The number of amino acids constituting the cyclic structure may be set at 8 or more to 20 or less, 10 or more to 20 or less, or 10 or more to 15 or less.

In the present invention, the cyclic peptide may be a modified one such as phosphorylated, methylated, acetylated, adenylylated, ADP-ribosylated, or glycosylated one. It may also be a cyclic peptide fused with another peptide or protein. It may also be a biotinylated one via an appropriate linker.

In the present invention, the cyclic peptide may be a dimer obtained by bonding two cyclic peptides each having one cyclic structure to each other via a linker structure and thereby having two cyclic structures in the molecule; or it may have an intramolecular lactam bridge structure obtained by intramolecularly forming a lactam structure.

No particular limitation is imposed on the linker structure for linking two cyclic peptides to each other and as a structure capable of linking peptides to each other, a linker having a structure known in the peptide synthesis field can be used.

The intramolecular lactam bridge structure may be formed by binding the respective side chains of the amino acids constituting the cyclic peptide. For example, an intramolecular lactam structure is formed by binding the side-chain amino group of Lys to the side-chain carboxyl group of Asp or Glu to form a peptide bond. The cyclic peptide has, in the molecule thereof, another cyclic structure as a bridge structure. Instead of Lys, for example, DAP, DAB, and Orn may be bound to Asp or Glu.

In the present invention, although the Plexin-binding regulating agent is not particularly limited insofar as it regulates binding between Semaphorin and Plexin and causes a change in cascade present downstream thereafter, the Plexin-binding regulating agent is preferably a Plexin A1 and/or Plexin B1 binding regulating agent and it is preferably a binding regulating agent between Semaphorin 3A and Plexin A1 or Semaphorin 4D and Plexin B1. The Plexin-binding regulating agent of the present invention may also be a binding inhibitor of Plexin by Semaphorin, more specifically, a binding inhibitor between Semaphorin 4D and Plexin B1. It may also be a Plexin activator, more specifically, a Plexin B1 activator.

The Plexin-binding regulating agent of the present invention may inhibit or accelerate activation of Plexin by Semaphorin, more specifically, may inhibit or accelerate activation of Plexin B1 by Semaphorin 4D.

It is known that when Semaphorin 4D binds to Plexin B1 on osteoblasts, it activates small G protein RhoA that inhibits differentiation of osteoblasts, reduces signals (IRS signals) that accelerate differentiation of osteoblasts, suppresses differentiation of osteoblasts, and thereby inhibits osteogenesis (WO2012/157237).

The Plexin-binding regulating agent of the present invention is expected to accelerate osteogenesis by inhibiting binding between Semaphorin 4D and Plexin B1 and it can be used for the treatment or prevention of diseases associated with bone metabolism.

Examples of the diseases associated with bone metabolism include bone fractures, bone deficiency, osteoporosis, osteomalacia, osteopenia, lumbar pain, Paget's disease of bone, tonic myelitis, articular rheumatism, and osteoarthrosis.

The Plexin-binding regulating agent of the present invention regulates binding between Semaphorin and Plexin, particularly, binding between Semaphorin 4D and Plexin B1 so that it can be used for the treatment or prevention of cancer.

Cancer diseases are not particularly limited and examples include various tumors such as pulmonary cancer, breast cancer, mesothelioma, carcinoma, glioma, and abnormal angiogenesis. The Plexin-binding regulating agent of the present invention can be used for the treatment or prevention of cancer as a cancer metastasis inhibitor.

The Plexin-binding regulating agent of the present invention regulates binding between Semaphorin and Plexin, particularly, binding between Semaphorin 4D and Plexin B1 so that it can be used for the treatment or prevention of neurodegenerative diseases such as Alzheimer disease, Parkinson's disease, central nervous system lesions, and demyelination due to lesions.

The Plexin-binding regulating agent of the present invention regulates binding between Semaphorin and Plexin, particularly, binding between Semaphorin 4D and Plexin B1 so that it can also be used for the treatment or prevention of neuroinflammatory diseases such as multiple sclerosis, amyotrophic lateral sclerosis, epilepsy, Alzheimer's disease, Parkinson's disease, meningitis, cerebral edema, brain damage, and cerebral stroke.

The Plexin-binding regulating agent of the present invention shows agonist activity in binding between Semaphorin and Plexin so that it can be used for treatment or prevention such as treatment of atopic dermatitis, inhibition of cancer metastasis, or inhibition of excessive immunoreaction in autoimmune diseases.

The Plexin-binding regulating agent of the present invention can be used not only as a therapeutic agent or preventive of diseases but also as a research tool for studying various roles of the interaction between Semaphorin and Plexin and it may be, for example, a research reagent.

The Plexin-binding regulating agent of the present invention can also be used as a diagnostic tool for determining an expression amount of Plexin in patient samples.

In the present invention, the cyclic peptide may be used as a pharmaceutically acceptable salt. Examples of the pharmaceutically acceptable salt of the cyclic peptide include salts of a pharmaceutically acceptable base or acid.

Specific examples of the pharmaceutically acceptable salt include addition salts of an inorganic acid (such as hydrochloric acid, hydrobromic acid, hydroiodic acid, sulfuric acid, or phosphoric acid), addition salts of an organic acid (such as p-toluenesulfonic acid, methanesulfonic acid, oxalic acid, p-bromophenylsulfonic acid, carboxylic acid, succinic acid, citric acid, benzoic acid, or acetic acid), inorganic bases (such as ammonium hydroxide, hydroxides of an alkali or alkaline earth metal, carbonates, or bicarbonates), and addition salts of an amino acid.

The cyclic peptide as the Plexin-binding regulating agent of the present invention is presumed to allosterically regulate the signal transmission particularly between Semaphorin 4D and Plexin B1 via its Arg-Trp-Thr structure so that it is not particularly limited insofar as it has the Arg-Trp-Thr structure. It has an amino acid sequence represented by one of the following Constructs:

Construct 1 comprising $(Xaa4)_m$, Arg-Trp-Thr, and $(Xaa5)_n$, wherein $(Xaa4)_m$ is attached to the Arg, and $(Xaa5)_n$ is attached to the Thr;

Construct 2 comprising Arg-Trp-Thr and $(Xaa5)_n$, wherein $(Xaa5)_n$ is attached to the Thr;

Construct 3 comprising $(Xaa4)_m$ and Arg-Trp-Thr, and $(Xaa5)_n$, wherein $(Xaa4)_m$ is attached to the Arg; and wherein Xaa4 and Xaa5 each independently represent an arbitrary amino acid, and m and n are each independently integers of 1 or more.

Xaa4 and Xaa5 constitute a cyclic structure and therefore, the cyclic peptide is obtained. The cyclic structure may be formed by binding of an N-terminal Xaa4 to a C-terminal Xaa5, binding of the N terminal Xaa4 to a non-C-terminal Xaa5, binding of a non-N-terminal Xaa4 to the C-terminal Xaa5, or binding of the non-N-terminal Xaa4 to the non-C-terminal Xaa5.

Xaa4 and Xaa5 may constitute a cyclic structure with a linker.

When the amino acid sequence is represented by Construct 2, Arg binds to Xaa5 and when the amino acid sequence is represented by Construct 3, Xaa4 binds to Thr.

In the present specification, when an amino acid represented by Xaa is 0, it means absence of an amino acid represented by Xaa. In the present specification, when amino acids represented by Xaa are two or more, it means that Xaa(s) are each independently selected from arbitrary amino acids. When the cyclic peptide has, for example, a structure represented by $(Xaa)_2$, two Xaa(s) may be the same amino acid or different amino acids.

Neither "m" nor "n" is particularly limited insofar as "m+n" becomes 1 or more. Preferably, "m" and "n" are each independently an integer selected so that "m+n" becomes 1 or more to 27 or less and within a range of 1 or more to 27 or less, "m" and "n" are selected as needed within a range of the number of amino acids constituting the cyclic structure.

The cyclic peptide may have a Val/Ile-Xaa1-Arg-Trp-Thr structure (SEQ ID NO: 42, wherein Xaa1 is an arbitrary amino acid) or may have an Arg-Trp-Thr-Xaa2-Xaa3-Ile/Val/Leu structure (SEQ ID NO: 43, wherein Xaa2 and Xaa3 each independently represent an arbitrary amino acid).

Further, the cyclic peptide may have a Val/Ile-Xaa1-Arg-Trp-Thr-Xaa2-Xaa3-Ile/Val/Leu structure (SEQ ID NO: 44, wherein Xaa1, Xaa2, and Xaa3 each independently represent an arbitrary amino acid).

Xaa2 preferably represents Gly.

In the present specification, the term "Val/Ile" in the cyclic peptide structure means Val or Ile. In the present specification, the term "Ile/Val/Leu" in the cyclic peptide structure means Ile, Val, or Leu, with Ile being preferred.

The cyclic peptide as the Plexin-binding regulating agent of the present invention is presumed to allosterically regulate the signal transmission particularly between Semaphorin 4D and Plexin B1 via its Leu-Ser-Trp structure so that the cyclic peptide is not particularly limited insofar as it is a cyclic peptide having a Leu-Ser-Trp structure. It has an amino acid sequence represented by one of the following Constructs:

Construct 4 comprising $(Xaa4)_m$, Leu-Ser-Trp, and $(Xaa5)_n$, wherein $(Xaa4)_m$ is attached to the Leu and $(Xaa5)_n$ is attached to the Trp;

Construct 5 comprising Leu-Ser-Trp, and $(Xaa5)_n$, wherein $(Xaa5)_n$ is attached to the Trp;

Construct 6 comprising $(Xaa4)_m$, and Leu-Ser-Trp, wherein $(Xaa4)_m$ is attached to the Leu;

wherein Xaa4 and Xaa5 each independently represent an arbitrary amino acid, and m and n are each independently integers of 1 or more.

Xaa4 and Xaa5 constitute a cyclic structure and therefore, the cyclic peptide is obtained. The cyclic structure may be formed by binding of an N-terminal Xaa4 to a C-terminal Xaa5, binding of the N terminal Xaa4 to a non-C-terminal Xaa5, binding of a non-N-terminal Xaa4 to the C-terminal Xaa5, or binding of the non-N-terminal Xaa4 to the non-C-terminal Xaa5.

Xaa4 and Xaa5 may constitute a cyclic structure via a linker.

When the amino acid sequence is represented by Construct 5, Leu binds to Xaa5 and when the amino acid sequence is represented by Construct 6, Xaa4 binds to Trp.

Neither "m" nor "n" is particularly limited insofar as "m+n" becomes 1 or more. Preferably, "m" and "n" are each independently an integer selected so that "m+n" becomes 1 or more to 27 or less and within a range of 1 or more to 27 or less, "m" and "n" are selected as needed within a range of the number of amino acids constituting the cyclic structure.

The cyclic peptide may have a Leu-Ser-Trp-Gln-Thr-Tyr-Ser structure (SEQ ID NO: 45).

The cyclic structure of the cyclic peptide may be formed by an N—CO—CH$_2$—S structure and this structure is preferably formed by binding of an acetyl group such as a chloroacetyl group obtained by substituting H of the acetyl group with a leaving group and a thiol group of cysteine of the C-terminal Xaa5 to the amino group of the N-terminal Xaa4. In this case, it preferably comprises an amino acid sequence represented by either one of the following constructs:

Construct 7 comprising XCH$_2$CO-Xaa6, Arg-Trp-Thr, and Cys, wherein the Xaa6 is linked to the Arg via bond or $-(Xaa7)_p-$, the Thr is linked to the Cys via a bond or $-(Xaa8)_q-$, and the Cys optionally comprises $(Xaa9)_r$ attached thereto; and Construct 8 comprising XCH$_2$CO-Xaa6, Leu-Ser-Trp, and Cys, wherein the Xaa6 is linked to the Leu via bond or $-(Xaa7)_p-$, the Trp is linked to the Cys via a bond or $-(Xaa8)_q-$, and the Cys optionally comprises $(Xaa9)_r$ attached thereto;

wherein p, q, and r are each independently positive integers, and Xaa6 to Xaa9 each independently represent an arbitrary amino acid.

Xaa6 to Xaa9 each independently represent an arbitrary amino acid and p+q number of Xaa7 and Xaa8 amino acid residues preferably falls within a range of 0 or more to 25 or less and is selected as needed within a range of the number of amino acids constituting the cyclic structure.

Xaa6 is preferably Trp and the C-terminal Xaa9 is preferably Gly or Ser. Although "r" is not particularly limited insofar as it stands for an integer of 1 or more, it may be 20 or less or may be 10 or less. It is preferably 1.

In the present specification, when "r" is an integer of 2 or more, $(Xaa9)_r$ in the cyclic peptide corresponds to a linear structure in which amino acids are linked by peptide bonding.

The cyclic peptide having a Val/Ile-Xaa1-Arg-Trp-Thr-Xaa2-Xaa3-Ile/Val/Leu structure (SEQ ID NO: 44) is represented preferably by the following construct:

Construct 9 comprising XCH$_2$CO-Xaa6, Val/Ile-Xaa1-Arg-Trp-Thr-Xaa2-Xaa3-Ile/Val/Leu (SEQ ID NO: 44), and Cys, wherein Xaa6 is linked to the N-terminus of SEQ ID NO: 44 via a bond or $-(Xaa10)_s-$, and the C-terminus of SEQ ID NO: 44 is linked to the Cys via a bond or $-(Xaa11)_t-$, and the Cys optionally comprises $(Xaa9)_r$ attached thereto, wherein s, t, and r are integers, and Xaa1 to Xaa3, Xaa6, and Xaa9 to Xaa11 are each independently an arbitrary amino acid;

More preferably Construct 9, wherein Xaa6 is Trp.

The cyclic structure of it is formed by an N—CO—CH$_2$—SN structure obtained by binding between the —CO—CH$_2$—X group that binds to the N-terminal Xaa6 or the amino group of Trp and the thiol group of Cys.

Xaa1 to Xaa3, Xaa6, and Xaa9 to Xaa11 are each independently an arbitrary amino acid and the "s+t" number of Xaa10 and Xaa11 amino acid residues preferably falls within a range of 0 or more to 20 or less and is selected as needed within a range of the number of amino acids constituting the cyclic structure.

Xaa6 is preferably Trp and the C-terminal Xaa9 is preferably Gys or Ser. Although "r" is not particularly limited insofar as it is an integer of 1 or more, it may be 20 or less or it may be 10 or less. It is preferably 1.

The cyclic peptide having a Leu-Ser-Trp-Gln-Thr-Tyr-Ser structure (SEQ ID NO: 45) is preferably represented by the construct:

Construct 10 comprising XCH$_2$CO-Xaa6, Leu-Ser-Trp-Gln-Thr-Tyr-Ser (SEQ ID NO: 45), and Cys, wherein Xaa6 is linked to the N-terminus of SEQ ID NO: 45 via a bond or $-(Xaa10)_s-$, and the C-terminus of SEQ ID NO: 45 is linked to the Cys via a bond or $-(Xaa12)_u-$, and the Cys optionally comprises $(Xaa9)_r$ attached thereto, wherein s, t, and r are integers, and Xaa6, Xaa9, Xaa10, and Xaa12 are each independently an arbitrary amino acid;

More preferably Construct 10, wherein Xaa6 is Trp.

Here, the cyclic structure is formed by an N—CO—CH$_2$—S structure obtained by binding between the —CO—CH$_2$—X group that binds to the N-terminal Xaa6 or the amino group of Trp and the thiol group of Cys.

Xaa6, Xaa9, Xaa10, and Xaa12 each independently represent an arbitrary amino acid and the "s+u" number of amino acid residues is preferably within a range of 0 or more to 21 or less and is selected as needed within a range of the number of amino acids constituting the cyclic structure.

Xaa6 is preferably Trp and the C-terminal Xaa9 is preferably Gly or Ser. Although "r" is not particularly limited insofar as it is an integer of 1 or more, it may be 20 or less or may be 10 or less. It is preferably 1.

The following are the specific examples of the cyclic peptide of the present invention.

[Chemical formula 1]

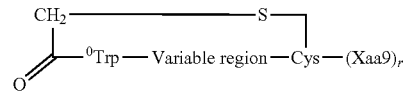

In the above structure, $^D$Trp means the D form of Trp and S means the thiol group of Cys. Xaa9 and "r" have the same meanings as described above.

Examples of Variable region in the above formula include:

RPRVARWTGQIIY, (SEQ ID NO: 30)
RVRVERWTGKLI, (SEQ ID NO: 31)
RPRVARWTGQIIH, (SEQ ID NO: 32)
RPRVARWTGQVIY, (SEQ ID NO: 33)
RPRVARWTGQNIY, (SEQ ID NO: 34)
RPRVARWTGQISN, (SEQ ID NO: 46)
RPRVARWTGQIIN, (SEQ ID NO: 36)
RPRAARWTGQIIY, (SEQ ID NO: 37)
RPYIERWTGRLIV, (SEQ ID NO: 47)
RWFYDRWTGTFYV, (SEQ ID NO: 48)
RAFIERWTGRLVV, (SEQ ID NO: 49)
LGYIARWTGTVVK, (SEQ ID NO: 50)
LAYIERWTGQIVR, (SEQ ID NO: 51)
NSNVLSWQTYSWY, (SEQ ID NO: 38)
NGRLSWQTYSHL, (SEQ ID NO: 52)
AVSNPPRPHYITIE, (SEQ ID NO: 28)
and
LSWQAYSWGQ. (SEQ ID NO: 41)

The cyclic peptide may have an amino acid sequence obtained by adding, substituting or deleting one or several, preferably 1 to 6, 1 to 5, 1 to 4, 1 to 3, or 1 or 2 amino acids to, with, or from the above-described amino acid sequences and have a binding regulating effect between Semaphorin and Plexin, preferably Semaphorin 4D and Plexin B1 insofar as it has an Arg-Trp-Thr structure or a Leu-Ser-Trp structure, preferably has a Val/Ile-Xaa1-Arg-Trp-Thr structure (SEQ ID NO: 42), more preferably has an Arg-Trp-Thr-Xaa2-Xaa3-Ile/Val/Leu structure (SEQ ID NO: 43), still more preferably has a Val/Ile-Xaa1-Arg-Trp-Thr-Xaa2-Xaa3-Ile/Val/Leu structure (SEQ ID NO: 44); or preferably has a Leu-Ser-Trp-Gln-Thr-Tyr-Ser structure (SEQ ID NO: 45).

The cyclic peptide may have an amino acid sequence having 70% or more, 80% or more, 90% or more, 95% or more, or 98% or more sequence identity to these amino acid sequences and have a binding regulating effect between Semaphorin and Plexin, preferably between Semaphorin 4D and Plexin B1 insofar as it has an Arg-Trp-Thr structure or a Leu-Ser-Trp structure, preferably has a Val/Ile-Xaa1-Arg-Trp-Thr structure (SEQ ID NO: 42), more preferably has an Arg-Trp-Thr-Xaa2-Xaa3-Ile/Val/Leu structure (SEQ ID NO: 43), more preferably a Val/Ile-Xaa1-Arg-Trp-Thr-Xaa2-Xaa3-Ile/Val/Leu structure (SEQ ID NO: 44); or preferably has a Leu-Ser-Trp-Gln-Thr-Tyr-Ser structure (SEQ ID NO: 45).

A method of producing the cyclic peptide of the present invention is not particularly limited and the cyclic peptide of the present invention can be produced using a known peptide synthesis technology.

Examples of the method of producing a cyclic peptide include a chemical synthesis method such as liquid-phase method, solid-phase method, or hybrid method using a liquid-phase method and a solid-phase method in combination; a gene recombination method, and a translation synthesis method in a cell-free translation system.

The cyclic peptide of the present invention can be produced suitably by a translation synthesis method in a cell-free translation system.

It can be produced by preparing a nucleic acid encoding the cyclic peptide and then translating the resulting nucleic acid in a cell-free translation system. The nucleic acid encoding a macrocyclic peptide can be designed as needed by those skilled in the art by using a genetic code used in an in vivo translation system, a reprogrammed genetic code, or a combination of them. The nucleic acid may be either DNA or RNA.

In accordance with the method using a cell-free translation system, not only a naturally occurring amino acid, but also a non-naturally occurring amino acid can be introduced efficiently into a peptide by using tRNA aminoacylated with the non-naturally occurring amino acid. For example, tRNA having an arbitrary anticodon can be aminoacylated with an arbitrary naturally occurring or non-naturally occurring amino acid by using artificial aminoacyl tRNA synthetase flexizyme developed by the present inventors. By using this technology, therefore, it is possible to reprogram a genetic code made of a mRNA triplet so that it encodes an amino acid different from that in a vivo translation system (WO2008/059823)

For example, an initiator codon AUG encodes formylmethionine and methionine in prokaryotic cells and eukaryotic cells, respectively. When flexizyme is used, on the other hand, tRNA corresponding to an initiator codon can be aminoacylated with another amino acid so that peptide synthesis can be initiated by an arbitrary amino acid. In addition, tRNA corresponding to a codon other than the initiator codon can be aminoacylated with an arbitrary amino acid so that an arbitrary amino acid can be introduced into an arbitrary position of a peptide by using a cell-free translation system.

Use of flexizyme enables binding of a hydroxy acid or carboxylic acid other than amino acid to tRNA so that an arbitrary hydroxy acid or carboxylic acid can be introduced into any position of a peptide by using a cell-free translation system. The cyclic peptide of the present invention may contain a hydroxy acid or carboxylic acid instead of an amino acid.

As flexizyme, for example, those described in the following documents are known.

H. Murakami, H. Saito, and H. Suga, (2003), Chemistry & Biology, Vol. 10, 655-662;

H. Murakami, D. Kourouklis, and H. Suga, (2003), Chemistry & Biology, Vol. 10, 1077-1084;

H. Murakami, A. Ohta, H. Ashigai, H. Suga (2006) Nature methods 3, 357-359;
N. Niwa, Y. Yamagishi, H. Murakami, H. Suga, (2009) Bioorganic & Medicinal Chemistry Letters 19, 3892-3894; and
WO2007/066627.

As flexizyme, original flexizyme (Fx) and altered ones thereof such as dinitrobenzyl flexizyme (dFx), enhanced flexizyme (eFx), and aminoflexizyme (aFx) are also known.

The aminoacylation method of an arbitrary tRNA with an arbitrary amino acid is not limited to a method using flexizyme and another method can also be applied to the present invention.

The cyclic peptide of the present invention having, at a desired position thereof, an amino acid necessary for the formation of a cycle or an amino acid constituting a cyclic structure and another structure can be obtained by making use of a technology using a cell-free translation system.

In this case, a codon encoding two amino acids necessary for forming a cycle (which may hereinafter be called "cycle-forming amino acids") and a codon encoding three amino acids corresponding to the Arg-Trp-Thr structure are introduced into a nucleic acid encoding the cyclic peptide.

A nucleic acid sequence may be determined so that it has, from the 5'-end, a codon encoding the cycle-forming amino acids, a codon encoding three amino acids corresponding to the Arg-Trp-Thr structure, and a codon encoding the cycle-forming amino acids arranged in order of mention and has an appropriate number of amino acids between these codons.

Although a method of cyclizing a peptide is not particularly limited, a cyclic peptide can be obtained, for example, by incorporating an amino acid having a functional group 1 shown below in Table 1 and an amino acid having a functional group 2 corresponding thereto in the peptide and cyclizing a translationally synthesized peptide by a spontaneous reaction.

Either the functional group 1 or 2 may be placed on the N-terminal side; they may be placed at the N-terminal and C-terminal, respectively; one of them may be a terminal amino acid and the other one may be a non-terminal amino acid; or both may be a non-terminal amino acid.

TABLE 1

| | Functional group 1 | | | Functional group 2 | |
|---|---|---|---|---|---|
| (A) | —C(=O)—CH$_2$—X$_1$ | (A-1) | | HS— | (A-2) |
| (B) | —C≡C—H | (B-1) | | N$_3$— | (B-2) |
| (C) | —Ar—CH$_2$NH$_2$ | (C-1) | | HO-indole | (C-2) |
| (D) | —C≡C—CH$_2$—X$_1$ | (D-1) | | HS— | (D-2) |
| (E) | —Ar—CH$_2$—X$_1$ | (E-1) | | HS— | (E-2) |

In the above formulas, Xi represents a leaving group, for example, a halogen atom such as Cl, Br, or I and Ar represents a substituted or unsubstituted aromatic ring.

As the amino acid having a functional group of (A-1), for example, a chloroacetylated amino acid can be used. Examples of the chloroacetylated amino acid include N-chloroacetyl-L-alanine, N-chloroacetyl-L-phenylalanine, N-chloroacetyl-L-tyrosine, N-chloroacetyl-L-tryptophan, N-3-(2-chloroacetamido)benzoyl-L-phenylalanine, N-3-(2-chloroacetamido)benzoyl-L-tyrosine, N-3-(2-chloroacetamido)benzoyl-L-tryptophan, β—N-chloroacetyl-L-diaminopropanoic acid, γ-N-chloroacetyl-L-diaminobutyric acid, σ-N-chloroacetyl-L-ornithine, and ε-N-chloroacetyl-L-lysine, and D-amino acid derivatives corresponding thereto.

As the amino acid having a functional group (A-1), N-chloroacetyl-L-tryptophan is preferably used, with D-form of it being more preferred.

In the present specification, it is sometimes described while showing clearly that the amino acid is L-form but it may be either L-form or D-form. Alternatively, it may be a mixture of L-form and D-form at any ratio. Even when it is described without clearly showing that the amino acid is L-form or D-form, it may be either L-form or D-form, or a mixture of L-form and D-form at any ratio.

Examples of the amino acid having a functional group (A-2) include cysteine, homocysteine, mercaptonorvaline, mercaptonorleucine, 2-amino-7-mercaptoheptanoic acid, and 2-amino-8-mercaptooctanoic acid.

As the amino acid having a functional group (A-1), cysteine is preferably used.

The cyclization method using the amino acid having a functional group (A-1) and the amino acid having a functional group (A-2) may be carried out according to the method described, for example, in Kawakami, T. et al., Nature Chemical Biology 5, 888-890 (2009); Yamagishi, Y. et al., ChemBioChem 10, 1469-1472 (2009); Sako, Y. et al., Journal of American Chemical Society 130, 7932-7934 (2008); Goto, Y. et al., ACS Chemical Biology 3, 120-129 (2008); and Kawakami T. et al, Chemistry & Biology 15, 32-42 (2008), and WO2008/117833.

As the amino acid having a functional group (B-1), for example, propargylglycine, homopropargylglycine, 2-amino-6-heptynoic acid, 2-amino-7-octynoic acid, and 2-amino-8-nonynoic acid can be used. In addition, 4-pentynoylated or 5-hexynoylated amino acids may also be used.

Examples of the 4-pentynoylated amino acid include N-(4-pentenoyl)-L-alanine, N-(4-pentenoyl)-L-phenylalanine, N-(4-pentenoyl)-L-tyrosine, N-(4-pentenoyl)-L-tryptophan, N-3-(4-pentynoylamido)benzoyl-L-phenylalanine, N-3-(4-pentynoylamido)benzoyl-L-tyrosine, N-3-(4-pentynoylamido)benzoyl-L-tryptophane, β-N-(4-pentenoyl)-L-diaminopropanoic acid, γ-N-(4-pentenoyl)-L-diaminobutyric acid, σ-N-(4-pentenoyl)-L-ornithine, and ε-N-(4-pentenoyl)-L-lysine, and D-amino acid derivatives corresponding thereto.

Examples of the 5-hexynoylated amino acid include amino acids obtained by substituting the 4-pentynoyl group of the compounds exemplified as the 4-pentynoylated amino acid by a 5-hexynoyl group.

As the amino acid having a functional group (B-2), for example, azidoalanine, 2-amino-4-azidobutanoic acid, azidoptonorvaline, azidonorleucine, 2-amino-7-azidoheptanoic acid, and 2-amino-8-azidooctanoic acid can be used.

In addition, azidoacetylated or 3-azidopentanoylated amino acid can also be used.

Examples of the azidoacetylated amino acid include N-azidoacetyl-L-alanine, N-azidoacetyl-L-phenylalanine, N-azidoacetyl-L-tyrosine, N-azidoacetyl-L-tryptophan, N-3-(4-pentynoylamido)benzoyl-L-phenylalanine, N-3-(4-pentynoylamido)benzoyl-L-tyrosine, N-3-(4-pentynoylamido)benzoyl-L-tryptophane, β-N-azidoacetyl-L-diaminopropanoic acid, γ-N-azidoacetyl-L-diaminobutyric acid, σ-N-azidoacetyl-L-ornithine, and ε-N-azidoacetyl-L-lysine, and D-amino acid derivatives corresponding thereto.

Examples of the 3-azidopentanoylated amino acid include amino acids obtained by substituting the azidoacetyl group of the compounds exemplified as the azidoacetylated amino acid by a 3-azidopentanoyl group.

The cyclization method of the amino acid having a functional group (B-1) and the amino acid having a functional group (B-2) can be performed according to the method described, for example, in Sako, Y. et al., Journal of American Chemical Society 130, 7932-7934 (2008) or WO2008/117833.

Examples of the amino acid having a functional group (C-1) include N-(4-aminomethyl-benzoyl)-phenylalanine (AMBF) and 3-aminomethyltyrosine.

Examples of the amino acid having a functional group (C-2) include 5-hydroxytryptophan (WOH).

Examples of the cyclization method using the amino acid having a functional group (C-1) and the amino acid having a functional group (C-2) include the method described in Yamagishi, Y. et al., ChemBioChem 10, 1469-1472 (2009) or WO2008/117833.

Examples of the amino acid having a functional group (D-1) include 2-amino-6-chloro-hexynoic acid, 2-amino-7-chloro-heptynoic acid, and 2-amino-8-chloro-octynoic acid.

Examples of the amino acid having a functional group (D-2) include cysteine, homocysteine, mercaptonorvaline, mercaptonorleucine, 2-amino-7-mercaptoheptanoic acid, and 2-amino-8-mercaptooctanoic acid.

Examples of the cyclization method using the amino acid having a functional group (D-1) and the amino acid having a functional group (D-2) include the method described in WO2012/074129.

Examples of the amino acid (E-1) include N-3-chloromethylbenzoyl-L-phenylalanine, N-3-chloromethylbenzoyl-L-tyrosine, and N-3-chloromethylbenzoyl-L-tryptophane and D-amino acid derivatives corresponding thereto.

Examples of an amino acid (E-2) include cysteine, homocysteine, mercaptonorvaline, mercaptonorleucine, 2-amino-7-mercaptoheptanoic acid, and 2-amino-8-mercaptooctanoic acid.

The cyclization method of the amino acid having the functional group (E-1) and the amino acid having the functional group (E-2) can be carried out referring to, for example, the cyclization method of (A-1) and (A-2) or the cyclization method of (D-1) and (D-2).

The ring-forming amino acid is preferably combination of the amino acid having a functional group (A-1) and the amino acid having a functional group (A-2), more preferably combination of N-acetyltryptophan having a leaving group as a substituent of H, still more preferably combination of an N-haloroacetyl-D-tryptophan, preferably, N-chloroacetyl-D-tryptophan and cystein.

The cyclic peptide of the present invention can be produced also by a solid-phase synthesis method.

As the solid-phase synthesis method, a method well known in the art and also publicly known can be used.

It will be described as exemplary. For example, an esterification reaction is performed between the hydroxyl group of a hydroxyl-containing resin and the carboxyl group of a first amino acid (usually, C-terminal amino acid of a target peptide) having an α-amino group protected with a protecting group. As an esterifying catalyst, usable is a known dehydration condensation agent such as 1-mesitylenesulfonyl-3-nitro-1,2,4-triazole (MSNT), dicyclohexylcarbodiimide (DCC), or diisopropylcarbodiimide (DIPCDI).

Then, the protecting group of the α-amino group of the first amino acid is eliminated and a second amino acid having all the functional groups protected except the main chain carboxyl group is added to activate the carboxyl group and bind the first and second amino acids to each other. Further, the protecting group of the α-amino group of the second amino acid is eliminated and a third amino acid having all the functional groups protected except the main chain carboxyl group is added to activate the carboxyl group and bind the second and third amino acids to each other. After the above-described reactions are repeated to synthesize a peptide having an intended length, all the functional groups are deprotected.

The method has been described in the case where the amino group of the amino acid is an α-amino group, but the method can also be performed in the case where the amino group of the amino acid is other than the α-amino group.

Examples of the resin for solid-phase synthesis include Merrifield resin, MBHA resin, Cl-Trt resin, SASRIN resin, Wang resin, Rink amide resin, HMFS resin, Amino-PEGA resin (Merck), and HMPA-PEGA resin (Merck).

Examples of the protecting group of the amino acid include a benzyloxycarbonyl (Cbz or Z) group, a tert-butoxycarbonyl (Boc) group, a fluorenylmethoxycarbonyl (Fmoc) group, a benzyl group, an allyl group, and an allyloxycarbonyl (Alloc) group.

Examples of the protecting group of the carboxyl group include methyl group, ethyl group, benzyl group, tert-butyl group, and cyclohexyl group.

With regards to another functional group of the amino group, examples of the hydroxy-protecting group of serine or threonine include benzyl group and tert-butyl group and examples of the hydroxy-protecting group of tyrosine include 2-bromobenzyloxycarbonyl group and tert-butyl group.

Protection and deprotection of the protecting group can be performed by the method described in Protective Groups In Organic Synthesis Second Edition by T. W. Greene and P. G. M. Wuts, John Wiley & Sons, Inc or based on this method.

The carboxyl group in the condensation reaction for forming amide bonds can be activated using a condensing agent. Examples of the condensing agent include dicyclohexylcarbodiimide (DCC), diisopropylcarbodiimide (DIPCDI), 1-ethyl-3-(3-dimethylaminopropyl)carbodiimide (EDC or WSC), (1H-benzotriazol-1-yloxy)tris(dimethylamino)phosphonium hexafluorophosphate (BOP), and 1-[bis(dimethylamino)methyl]-1H-benzotriazolium-3-oxide hexafluorophosphate (HBTU).

A peptide chain can be cleaved from the solid-phase resin by treating it with an acid such as TFA or hydrogen fluoride (HF).

The Plexin-binding regulating agent of the present invention can be used as a pharmaceutical composition.

The administration route of the pharmaceutical composition is not particularly limited and it may be administered either orally or parenterally. Examples of the parenteral administration include administration by injection such as intramuscular, intravenous, or subcutaneous injection, transdermal administration, and transmucosal administration.

Examples of the transmucosal administration route include nasal, buccal, ocular, pulmonary, vaginal, and rectal administration routes.

From the standpoint of drug kinetics such as metabolism or excretion, the cyclic peptide in the pharmaceutical composition can be subjected to various modifications. For example, the cyclic peptide can have a longer residence time in blood and reduced antigenicity by adding thereto polyethylene glycol (PEG) or sugar chain.

The cyclic peptide may be encapsulated using a sustained-release base such as an emulsion, nanoparticles, nanospheres, or the like prepared from a biodegradable polymer compound such as polylactic acid glycol (PLGA), porous hydroxyapatite, liposome, surface-modified liposome, or unsaturated fatty acid. In the case of transdermal administration, the pharmaceutical composition can be penetrated through the stratum corneum by passing a weak electrical current through the skin surface (iontophoresis).

As the pharmaceutical composition, the cyclic peptide may be used as is as the active ingredient or its preparation may be obtained by adding thereto a pharmaceutically acceptable additive or the like.

Examples of the dosage form of the pharmaceutical preparation include liquids and solutions (for example, injections), dispersions, suspensions, tablets, pills, powders, suppositories, powders, fine granules, granules, capsules, syrups, troches, inhalants, ointments, ophthalmic preparations, nasal preparations, ear preparations, and cataplasms.

The preparation can be obtained in a conventional manner by using, for example, an excipient, a binder, a disintegrant, a lubricant, a dissolving agent, a solubilizing agent, a colorant, a taste/odor corrigent, a stabilizer, an emulsifier, an absorption promoter, a surfactant, a pH regulator, an antiseptic, a humectant, a dispersant, or an antioxidant as needed.

Examples of the additive to be used for obtaining the preparation include, but not limited to, purified water, saline, phosphate buffer, pharmaceutically acceptable organic solvents such as dextrose, glycerol, and ethanol, animal or vegetable oils, lactose, mannitol, glucose, sorbitol, crystalline cellulose, hydroxypropyl cellulose, starch, corn starch, silicic anhydride, magnesium aluminum silicate, collagen, polyvinyl alcohol, polyvinylpyrrolidine, carboxyvinyl polymer, carboxymethylcellulose sodium, sodium polyacrylate, sodium alginate, water-soluble dextran, carboxymethyl starch sodium, pectin, methyl cellulose, ethyl cellulose, xanthan gum, gum arabic, tragacanth, casein, agar, polyethylene glycol, diglycerin, glycerin, polypropylene glycol, petrolatum, paraffin, octyl dodecyl myristate, isopropyl myristate, higher alcohol, stearyl alcohol, stearic acid, and human serum albumin.

Examples of the absorption promoter in transmucosal absorption include surfactants such as polyoxyethylene lauryl ethers, sodium lauryl sulfate, and saponin; salts of a bile acid such as glycocholate, deoxycholate, and taurocholate; chelating agents such as EDTA and salicylic acid; fatty acids such as caproic acid, capric acid, lauric acid, oleic acid, linoleic acid, and mixed micelle; enamine derivatives, N-acylcollagen peptides, N-acylaminoic acids, cyclodextrines, chitosans, and nitric oxide donors.

Pills or tablets may be tablets coated with sugar, gastric-soluble substance, enteric substance, or the like.

Liquids and solutions may contain distilled water for injection, physiological saline, propylene glycol, polyethylene glycol, a vegetable oil, an alcohol, or the like. It may further contain a humectant, an emulsifier, a dispersant, a stabilizer, a dissolving agent, a solubilizing agent, an antiseptic, or the like.

The present invention also provides a method of administering the Plexin-binding regulating agent, preferably, a binding regulating agent between Semaphorin 4D and Plexin B1 to a patient requiring the regulating agent and thereby treating or preventing the disease of the patient.

The dose of the Plexin-binding regulating agent of the present invention, preferably, a binding regulating agent between Semaphorin 4D and Plexin B1 can be determined as needed by those skilled in the art, depending on the symptom, age, sex, weight, or sensitivity difference of a patient requiring the regulating agent, an administration method, an administration interval, a kind of the preparation, or the like.

The patient is a mammal, preferably a human being.

EXAMPLES

The present invention will hereinafter be described specifically by Examples but the present invention is not limited to or by the following examples.

Cyclic peptides to be bound to Plexin B1 were obtained by performing a RaPID system for the N-terminal head piece of human Plexin B1. Cyclic peptides categorized into four families were obtained by the selection using the RaPID system repeated five times or more.

The respective amino acid sequences of the cyclic peptides are shown in FIG. 1.

The cyclic peptides shown in FIG. 1c were obtained by chemical synthesis and binding affinity to Plexin B1 was analyzed by surface resonance plasmon (SPR).

Figure 2:
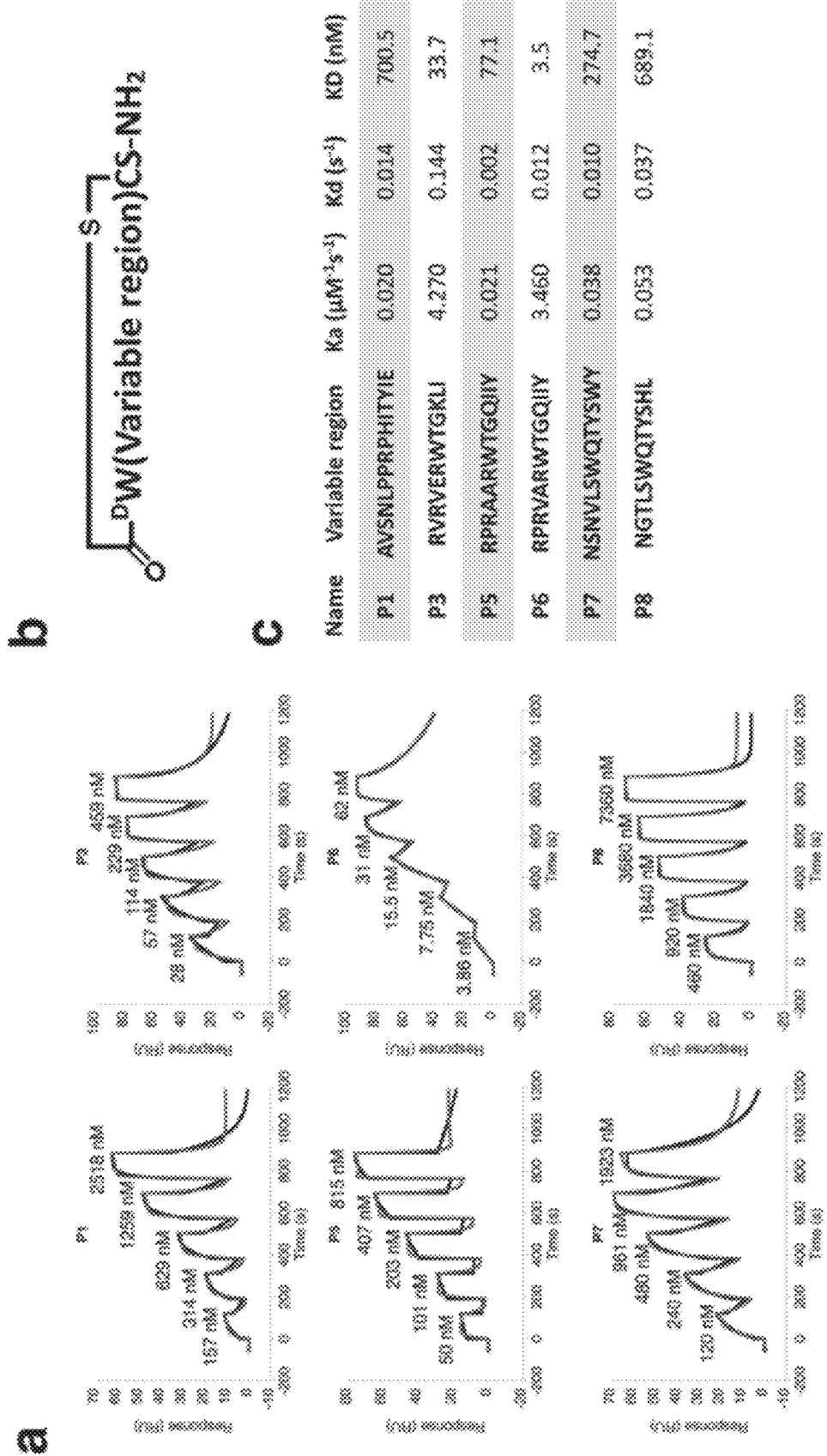
FIG. 2a shows the surface resonance plasmon (SPR) analysis results of binding of a chemically synthesized cyclic peptide to Plexin B1.

As shown in FIG. 2c, they indicate a dissociation constant (KD) of nM order.

In addition, the binding affinity of the cyclic peptides shown below in Table 2 to human and mouse Plexin B1 was analyzed similarly. The cyclic peptides shown in Table 2 also indicate a dissociation constant (KD) of nM order in mouse Plexin B1. In Table 2, w means ° W in the cyclic peptide shown in FIG. 2b. In the cyclic peptide shown in FIG. 2b, Ser binds to C, which is Cys, while in the cyclic peptides shown in Table 2 and other than cyclic peptide P6, Gly binds to C.

TABLE 2

|  |  | KD (nM) | |
| --- | --- | --- | --- |
|  |  | Human | Mouse |
| P6 | wRPRVARWTGQITYC | 2.77 |  |
| mp6-9 | wRPYIERWTGRLTVC | 0.28 | 43.6 |
| mp6-2 | wRWFYDRWTGTFYVC |  | 59 |
| mp6-7 | wRAFIERWTGRLVVC | 4.58 | 126 |
| mp6-3 | wLGYIARWTGTVVKC | 241 | 227 |
| mp6-5 | wLAYIERWTGQIVRC | 173.6 | 507 | wherein the sequences from top to bottom are SEQ ID NO: 53 to SEQ ID NO: 58, respectively.

Figure 3:
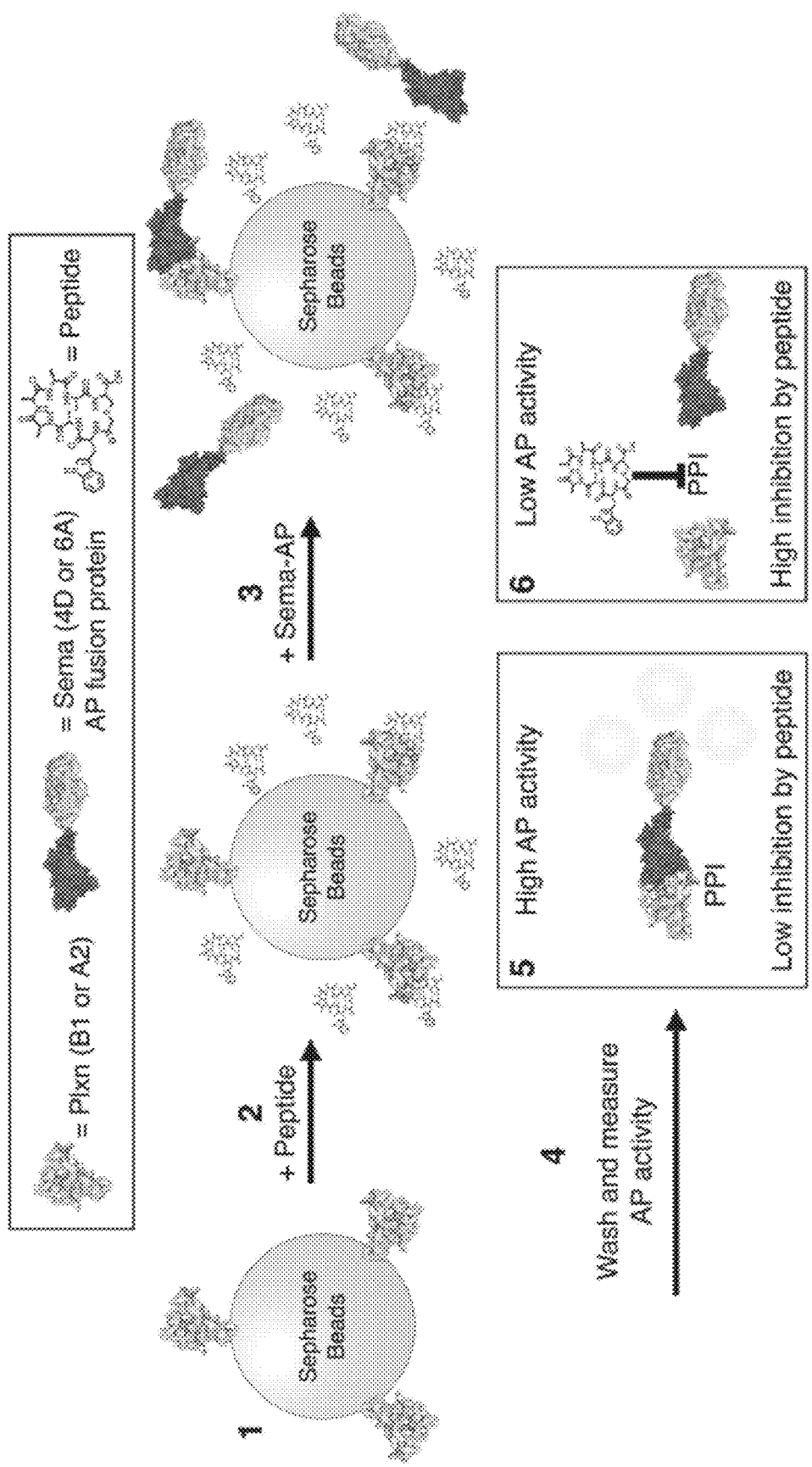
FIG. 3 shows a schematic view of the binding assay between Semaphorin 4D and Plexin B1.

The effect of the cyclic peptides shown in FIG. 2c on protein-protein interaction (PPI) of Plexin B1 and Semaphorin 4D was studied by in vitro pulldown assay (FIG. 3).
1. Plexin B1 or Plexin A2 was immobilized on Sepharose beads.
2. A cyclic peptide that bound to Plexin B1, a negative control peptide, or dimethylsulfoxide (DMSO) was added to Plexin-B1-immobilized beads.
3. An alkali phosphatase (AP)-fused protein of Semaphorin 4D or Semaphorin 6A was added.
4. After washing of the resulting beads, an increase in absorbance of the sample was measured at 405 nm to determined AP activity.

High AP activity relates to high interaction (5) between Semaphorin and Plexin and low AP activity relates to high interaction (6) between Semaphorin and Plexin.

Figure 4:
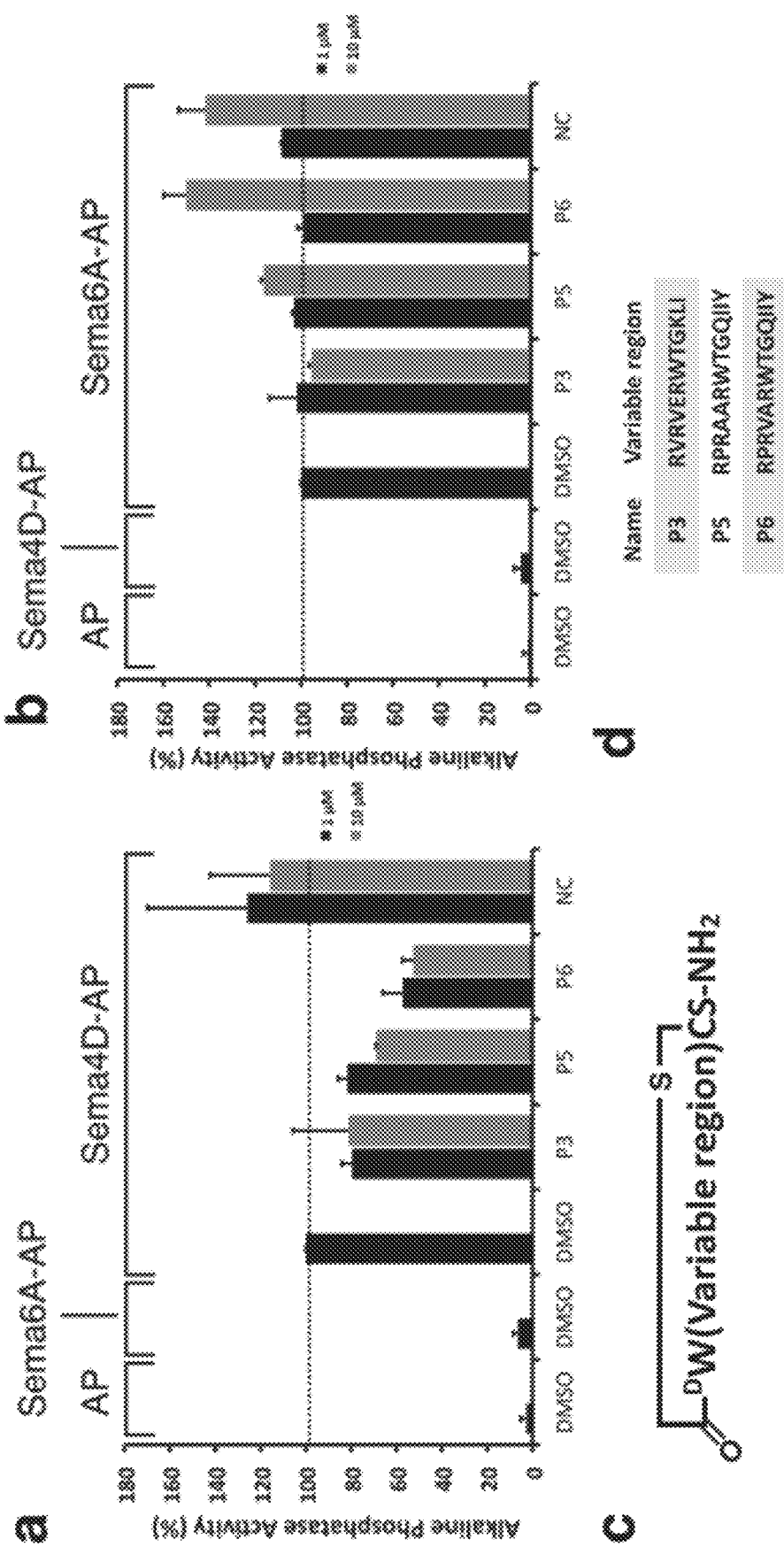
FIG. 4a shows the results of the binding assay between Semaphorin 4D and Plexin B1 and FIG. 4b shows the results of the binding assay between Semaphorin 6A and Plexin A2.
FIG. 4c is the general formula of cyclic peptides and FIG. 4d shows the respective amino acid sequences of the cyclic peptides. The sequences from top to bottom are SEQ ID NO: 31, SEQ ID NO: 37, and SEQ ID NO: 30.
Figure 5:
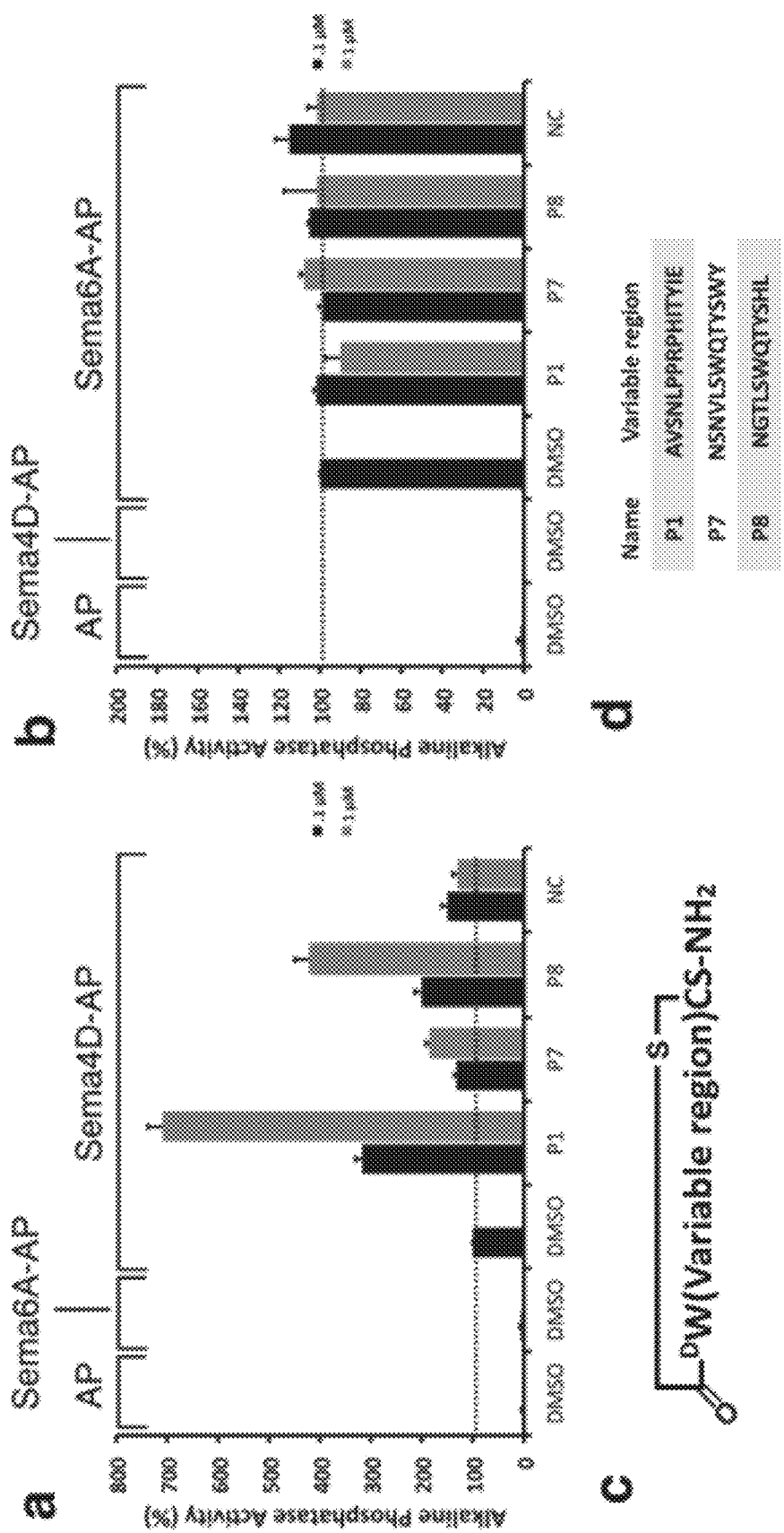
FIG. 5a shows the results of the binding assay between Semaphorin 4D and Plexin B1 and FIG. 5b shows the results of the binding assay between Semaphorin 6A and Plexin A2.
FIG. 5c is the general formula of cyclic peptides and FIG. 5d shows the respective amino acid sequences of the cyclic peptides. The sequences from top to bottom are SEQ ID NO: 40, SEQ ID NO: 38, and SEQ ID NO: 39.

The results are shown in FIGS. 4 and 5. The cyclic peptides shown in FIGS. 4c and d inhibit the interaction between Plexin B1 and Semaphorin 4D and the cyclic peptides shown in FIGS. 5c and d enhance the interaction between Plexin B1 and Semaphorin 4D.

As the result of measurement of the AP activity of the cyclic peptides shown in Table 2, the cyclic peptide mp6-9 showed the interaction inhibiting activity between human Plexin B1 and Semaphorin 4D equivalent to that of the cyclic peptide P6. The cyclic peptide mp6-2 showed the interaction inhibiting activity between mouse Plexin B1 and Semaphorin 4D equivalent to that of the cyclic peptide P6. The cyclic peptides mp6-9 and mp6-3 showed stronger inhibiting activity than the cyclic peptide P6.

Figure 6:
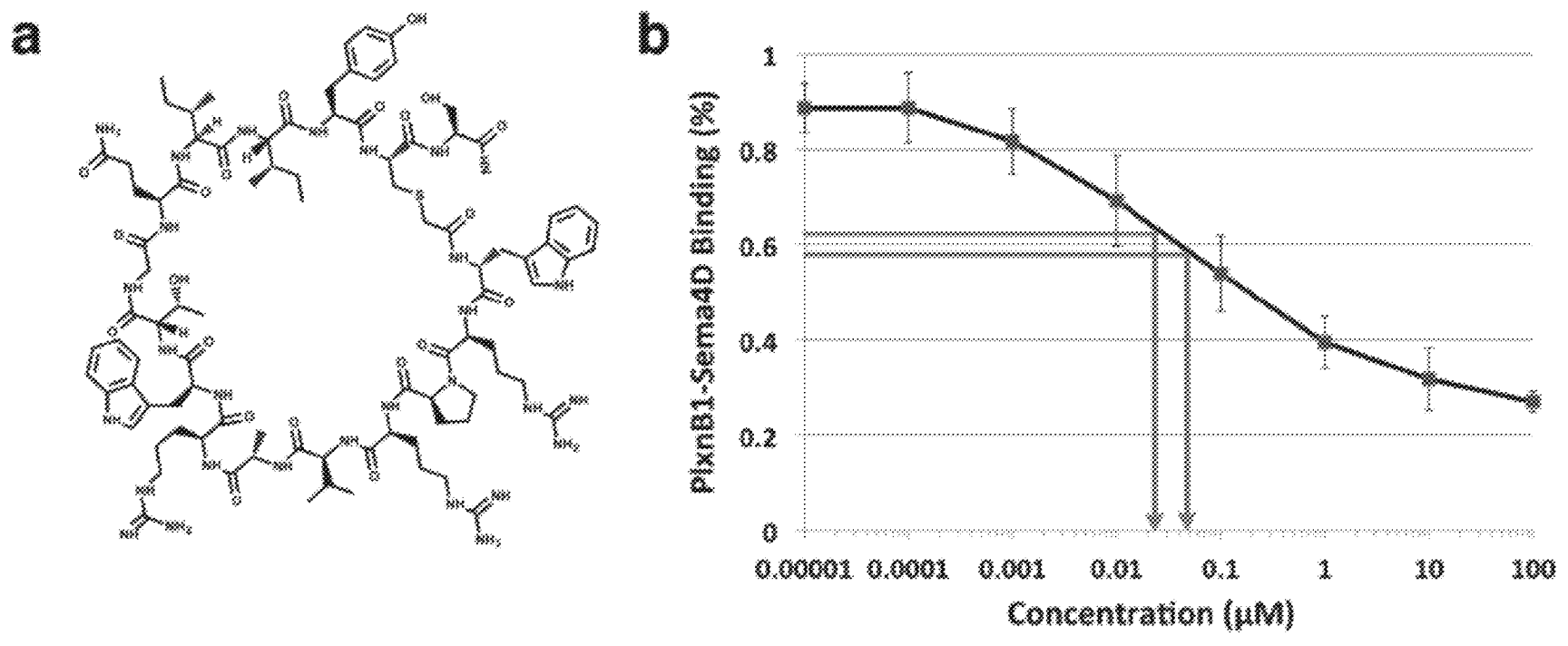

The Plexin PPI inhibiting activity of the cyclic peptide P6 was measured at each concentration. The results are shown in FIG. 6.

Figure 7:
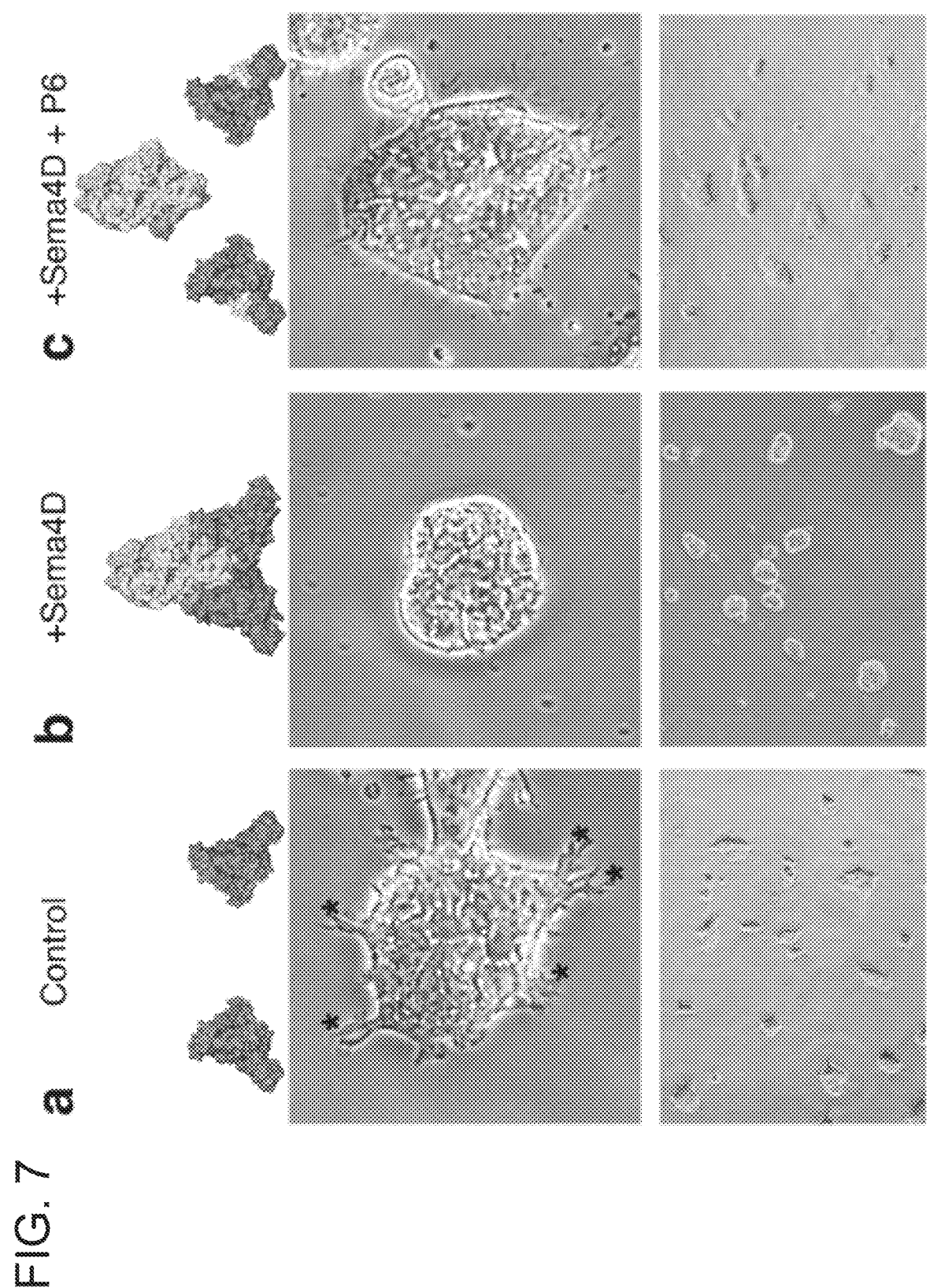
FIG. 7 shows the results of a collapse test of a dendrite, which is called "growth cone", of exogenously Plexin-B1 expressing cells HEK239.

An inhibition test of growth cone collapse depending on Semaphorin 4D was performed using exogenously Plexin B1-expressing cells HEK293. The results are shown in FIG. 7.

Figure 8:
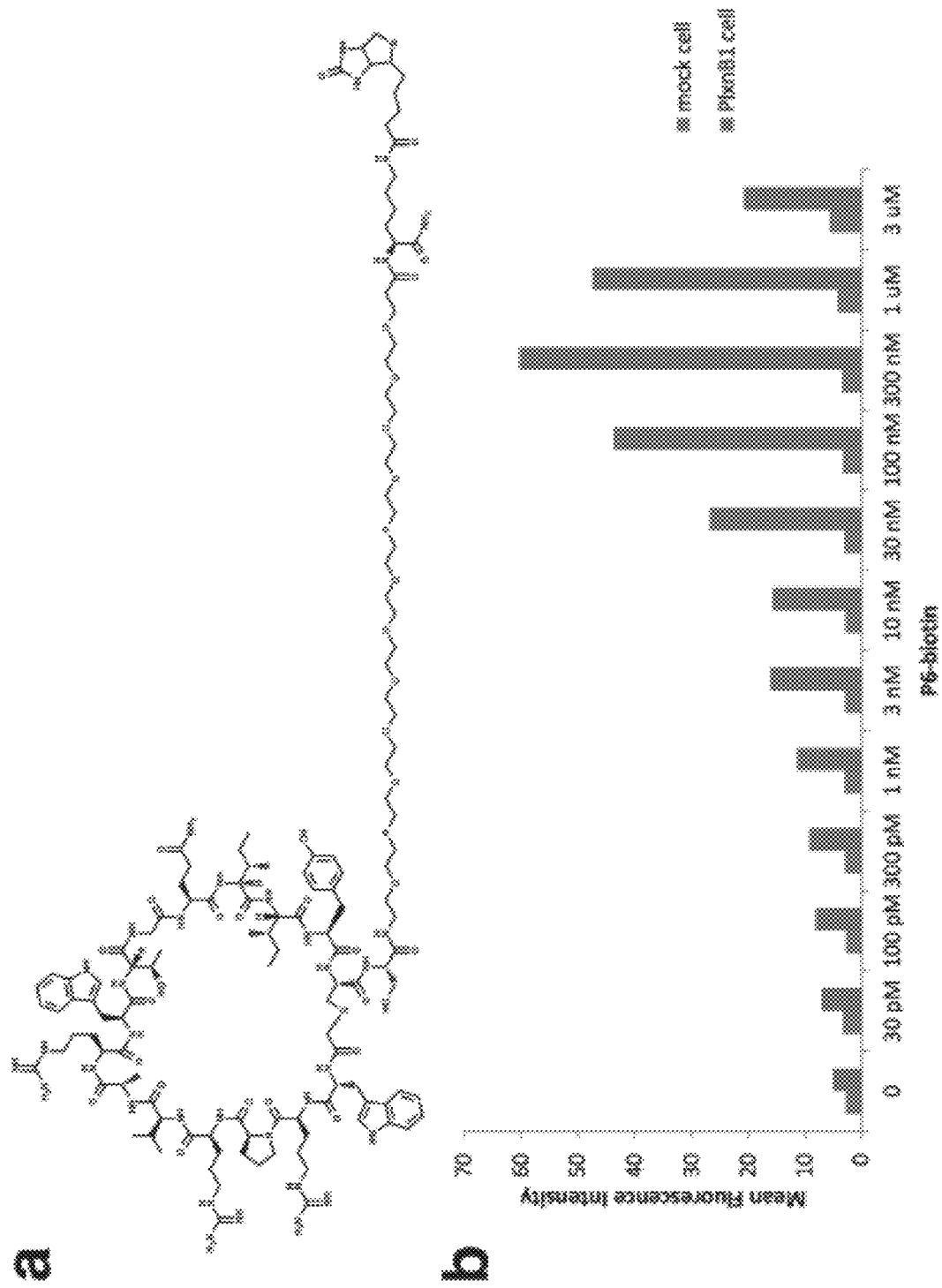
FIG. 8a shows a biotin-bound cyclic peptide P6.
FIG. 8b shows the fluorescence labeling results in Plexin B1-expressing HEK239 cells to which the biotin-bound cyclic peptide P6 has been added.

The cyclic peptide P6 was biotinylated by the conventional method. The structure of the biotinylated cyclic peptide P6 is shown in FIG. 8a.

The biotinylated P6 thus synthesized was added to mock cells not expressing Plexin B1 and HEK239 cells exogenously expressing Plexin and then, streptavidin-PE was added to determine its binding amount by FACS (fluorescence activated cell sorting). The results are shown in FIG. 8b.

Further, SPR analysis was performed for testing the role of each amino acid of P6 in binding between the cyclic peptide P6 and Plexin B1.

Figure 9:
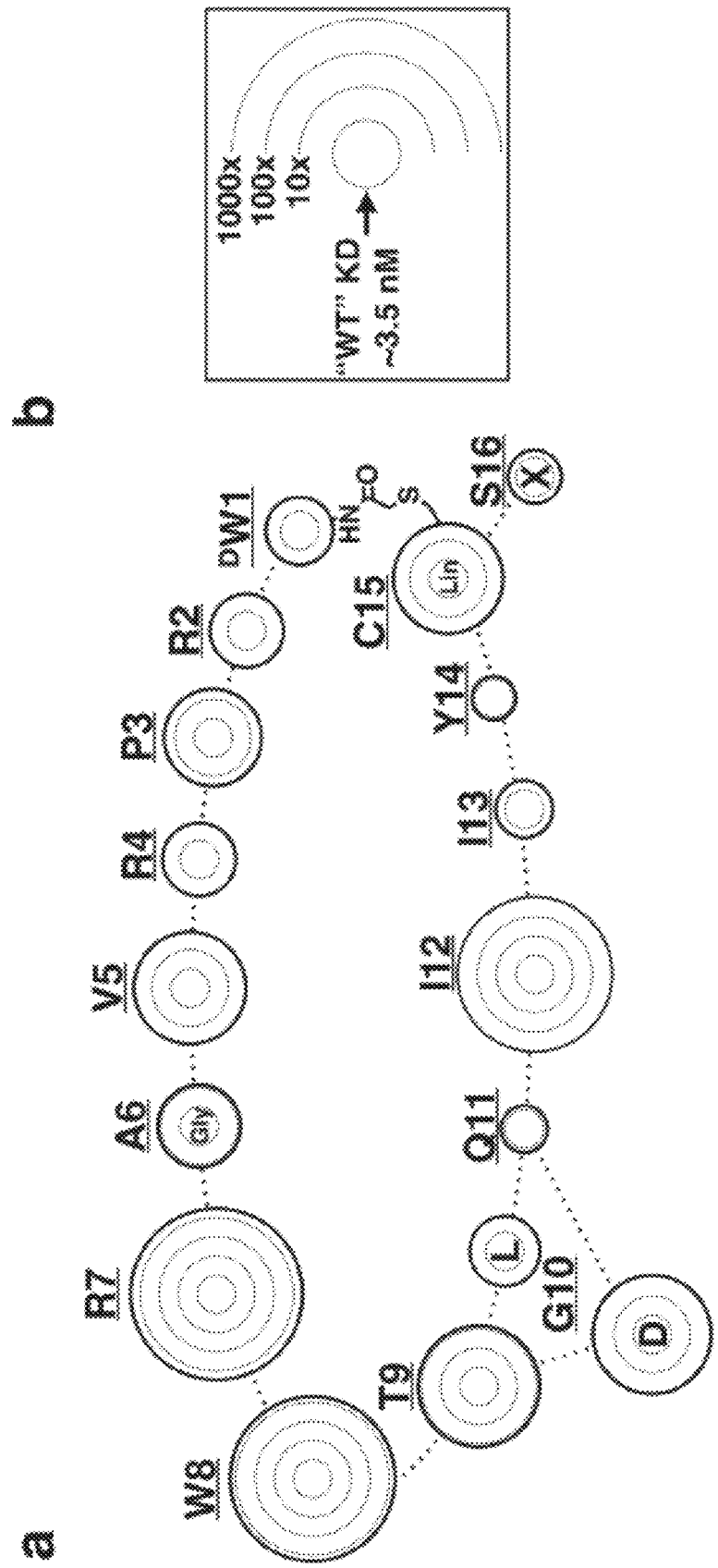
FIG. 9 shows the influence of alanine mutagenesis of the cyclic peptide P6 on Plexin B1 binding ability which is indicated by an increase in the KD value determined by SPR.

The present SPR analysis succeeded in finding an amino acid residue essential in the binding between the cyclic peptide and Plexin B1. As shown in FIG. 9, in P6, R7, W8 and T9 were important for the binding between the cyclic peptide and Plexin B1. This means that the cyclic peptide when it has an Arg-Trp-Thr structure can function as a binding regulating agent between Semaphorin 4D and Plexin B1.

Figure 11:
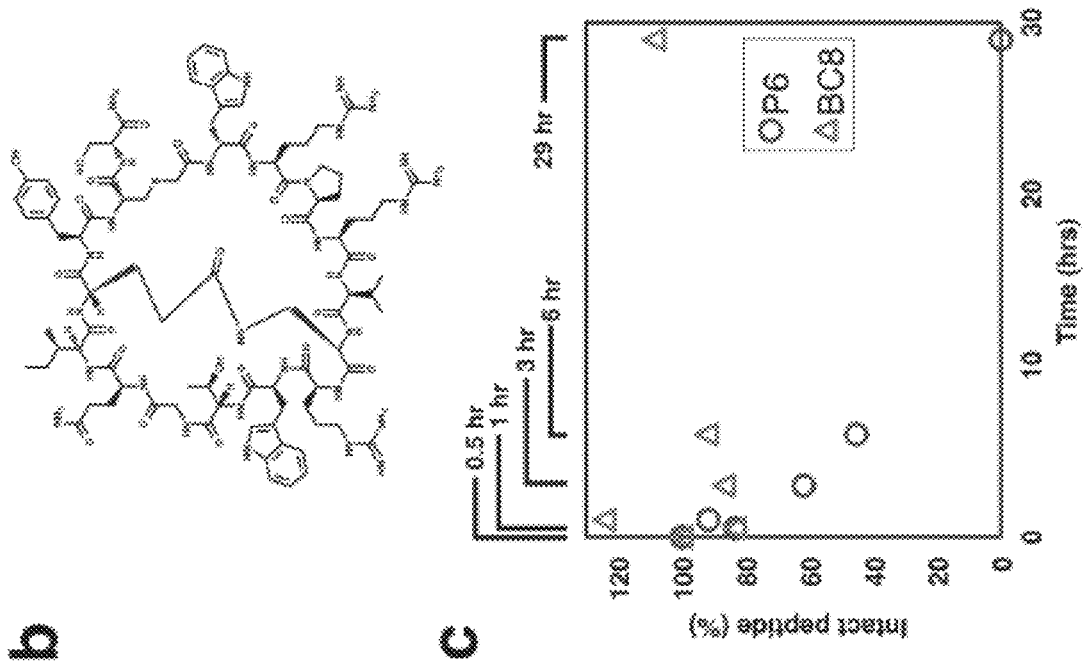
FIG. 11a shows the SPR analysis results of cyclic peptides having an intramolecular lactam bridge structure.
FIG. 11b shows the structure of a cyclic peptide BC8.
FIG. 11c shows the half-life due to degradation by the serum protease.

For comparison with the cyclic peptide P6, a cyclic peptide having an intramolecular lactam bridge structure as shown in FIG. 10 was chemically synthesized and its binding affinity to Plexin B1 was analyzed by surface resonance plasmon (SPR) (FIG. 11a).

A stability test, with serum protease, of the cyclic peptide P6 and the cyclic peptide having an intramolecular lactam bridge structure was performed (FIG. 11c). P6 showed a half-life of from 3 to 6 hours, while the cyclic peptide BC8 having an intramolecular lactam bridge structure was not decomposed even after 29 hours.

Figure 12:
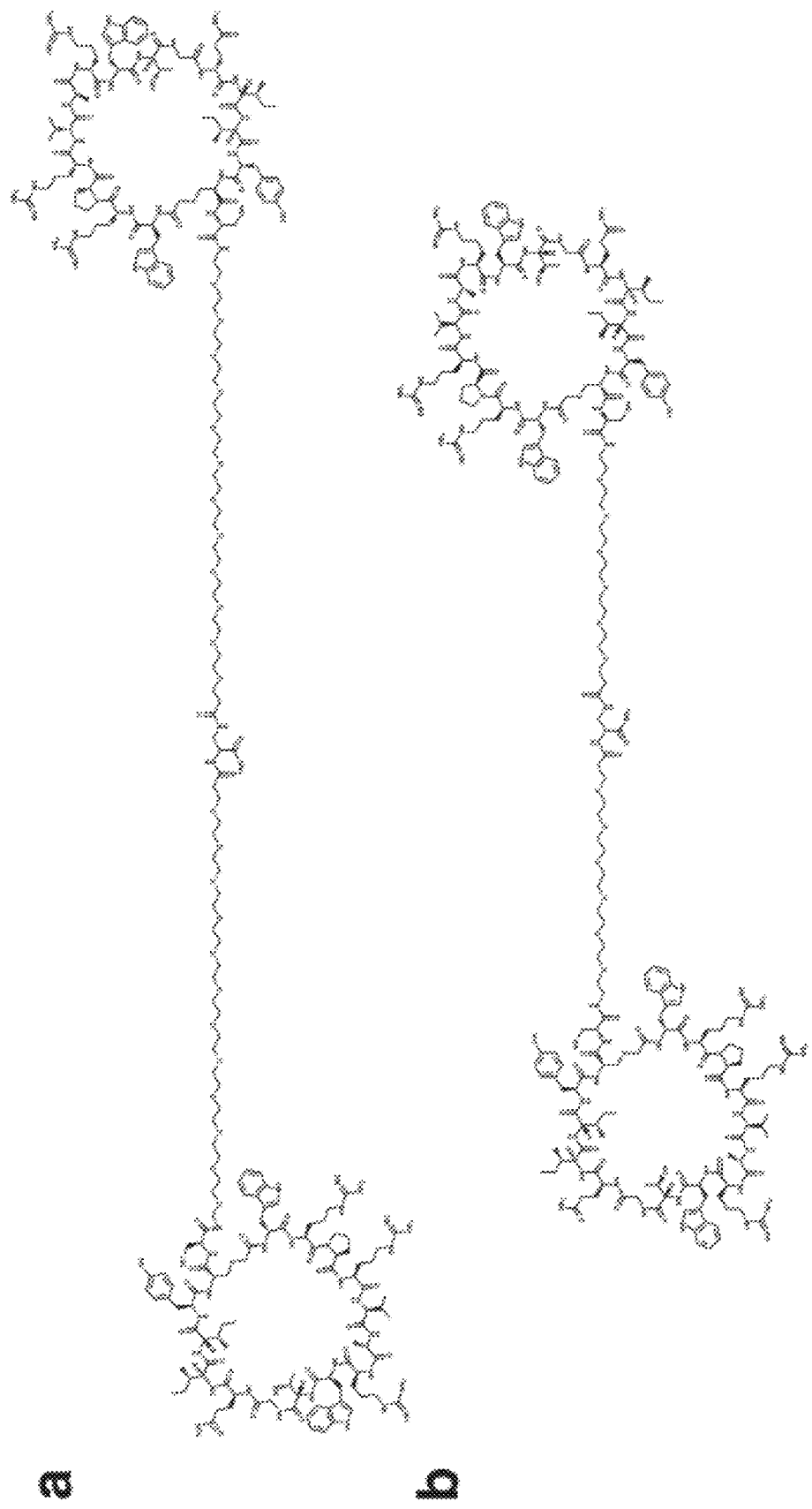
FIG. 12 shows the dimers of the cyclic peptide P6.
Figure 13:
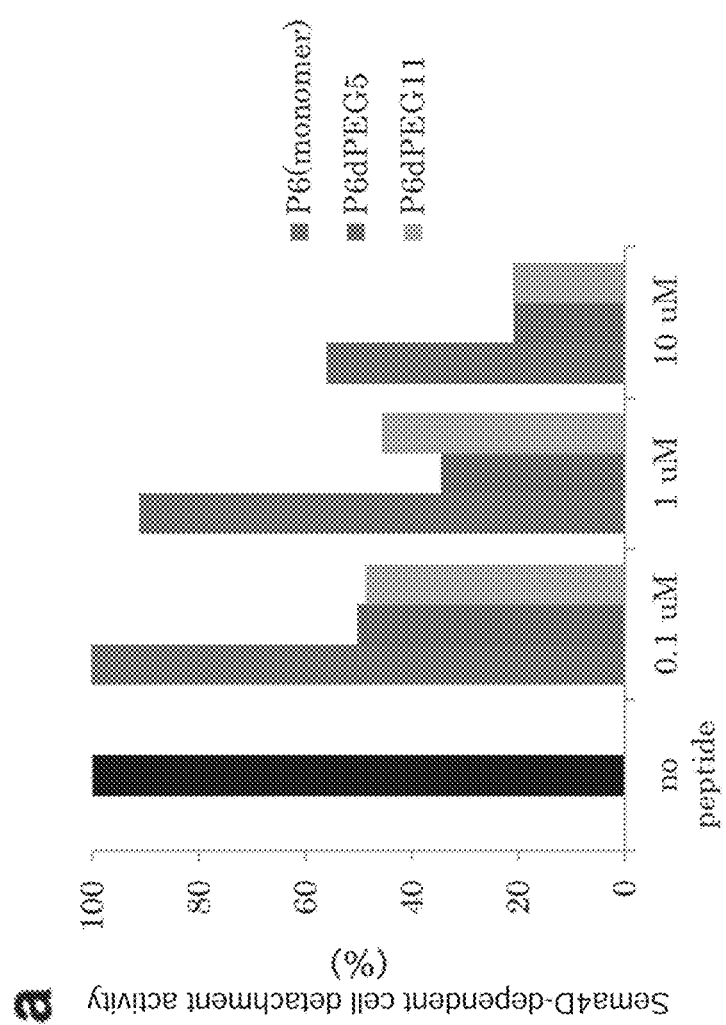
FIG. 13 shows comparison in activity between the cyclic peptide P6 and the dimers of P6.

The cyclic peptide P6 was dimerized by the conventional method. The respective structures of the dimerized cyclic peptides P6 (P6dPEG5 and P6dPEG11) are shown in FIG. 12. An inhibition test of each peptide against cell detachment by the stimulation of Semaphorin 4D was performed using the dimerized peptide shown in FIG. 12 and exogenously Plexin-B1 expressing cells HEK293. The results are shown in FIG. 13.

As the result of Collapse assay using xCELLigence (ACEA Biosciences Inc.), it has been observed that P-7 PEG dimers (P7dPEG5 and P7dPEG11) obtained by dimerizing a cyclic peptide P7 in a manner similar to that of the dimerized cyclic peptide P6 having a structure shown in FIG. 12 specifically cause a Sema-4D-like collapse effect on the Plexin-B1 expressing cells, in other words, they are effective for accelerating activation of Plexin B1.

What is claimed is:

1. A method of regulating a binding of a Plexin B1, which comprises contacting the Plexin B1 with a cyclic peptide comprising a sequence selected from the group consisting of: SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, and SEQ ID NO: 35,
or a pharmaceutically acceptable salt of the cyclic peptide or a pharmaceutical composition thereof.

2. The method of regulating according to claim 1, wherein the binding is an interaction between the Plexin B1 and a semaphorin.

3. The method according to claim 1, wherein the cyclic peptide has an N—CO—CH$_2$—S structure, wherein N is nitrogen and S is sulfur.

4. The method according to claim 3, wherein the N is the nitrogen atom in the amino group of a tryptophan residue.

5. The method according to claim 3, wherein the S is the sulfur atom of a cysteine residue.

6. The method according to claim 1, wherein the cyclic peptide has a cyclic structure having up to 20 amino acids.

7. The method according to claim 1, wherein the cyclic peptide has an intramolecular lactam bridge structure.

8. The method according to claim 1, wherein the cyclic peptide is a dimer.

9. The method according to claim 1, wherein the cyclic peptide is in the form of a pharmaceutical composition.

* * * * *